(12) United States Patent  (10) Patent No.: US 8,029,503 B2
Sretavan                        (45) Date of Patent:      Oct. 4, 2011

(54) NERVE REPAIR BY SELECTIVE SURGICAL REPAIR OF AXONS

(75) Inventor: David Sretavan, Tiburon, CA (US)

(73) Assignee: The Regents of the University of California, Oakland, CA (US)

( * ) Notice: Subject to any disclaimer, the term of this patent is extended or adjusted under 35 U.S.C. 154(b) by 1237 days.

(21) Appl. No.: 10/575,569

(22) PCT Filed: Oct. 12, 2004

(86) PCT No.: PCT/US2004/033784
§ 371 (c)(1),
(2), (4) Date: Oct. 24, 2006

(87) PCT Pub. No.: WO2005/037070
PCT Pub. Date: Apr. 28, 2005

(65) Prior Publication Data
US 2007/0067883 A1    Mar. 22, 2007

Related U.S. Application Data

(60) Provisional application No. 60/510,788, filed on Oct. 11, 2003.

(51) Int. Cl.
*A61B 17/36* (2006.01)
*A61B 17/32* (2006.01)
(52) U.S. Cl. .......................................... 606/22; 607/62
(58) Field of Classification Search .................. 606/22, 606/152, 41; 607/62, 48; 514/352, 723
See application file for complete search history.

(56) References Cited

U.S. PATENT DOCUMENTS

| 4,306,561 | A | * | 12/1981 | de Medinaceli | 606/22 |
| 4,632,116 | A | * | 12/1986 | Rosen et al. | 607/62 |
| 5,416,657 | A |   | 5/1995 | Beck et al. | |
| 5,645,684 | A |   | 7/1997 | Keller | |
| 5,651,900 | A |   | 7/1997 | Keller et al. | |
| 5,792,137 | A |   | 8/1998 | Carr et al. | |
| 5,893,974 | A |   | 4/1999 | Keller et al. | |
| 5,948,255 | A |   | 9/1999 | Keller et al. | |
| 6,015,599 | A |   | 1/2000 | Keller et al. | |
| 6,106,751 | A |   | 8/2000 | Talbot et al. | |
| 6,125,007 | A |   | 9/2000 | Beck et al. | |
| 7,582,680 | B1 | * | 9/2009 | Shi et al. | 514/723 |

OTHER PUBLICATIONS

Archer S, Morgan H, Rixon FJ (1999) "Electrorotation studies of baby hamster kidney fibroblasts infected with herpes simplex virus type 1," *Biophys J* 76:2833-2842.

Blakemore WF, Franklin RJ (2000) "Transplantation options for therapeutic central nervous system remyelination," *Cell Transplant* 9:289-294.

(Continued)

*Primary Examiner* — Vy Q Bui
(74) *Attorney, Agent, or Firm* — Quine Intellectual Property Law Group P.C.; Stephen J. LeBlanc

(57) ABSTRACT

Method and systems for nerve repair and for microfabrication. In specific embodiments, nerve repair is accomplished by repairing axons. In further embodiments, a modular, 3D system having very small dimentions is described. In further embodiments, a method ans system for performing surgery on axons is disclosed.

20 Claims, 26 Drawing Sheets

OTHER PUBLICATIONS

Coumans JV, Lin TT, Dai HN, MacArthur L, McAtee M, Nash C, Bregman BS (2001) "Axonal regeneration and functional recovery after complete spinal cord transection in rats by delayed treatment with transplants and neurotrophins," *J Neurosci* 21:9334-9344.

Heida T, Rutten WL, Marani E (2001) "Dielectrophoretic trapping of dissociated fetal cortical rat neurons," *IEEE Trans Biomed Eng* 48:921-930.

Heida T, Rutten WL, Marani E (2002) "Experimental investigation on neural cell survival after dielectrophoretic trapping," *Arch Physiol Biochem* 110:373-382.

Lore AB, Hubbell JA, Bobb DS, Jr., Ballinger ML, Loftin KL, Smith JW, Smyers ME, Garcia HD, Bittner GD (1999) "Rapid induction of functional and morphological continuity between severed ends of mammalian or earthworm myelinated axons," *J Neurosci* 19:2442-2454.

Ogata S, Yasukawa T, Matsue T (2001) "Dielectrophoretic manipulation of a single chlorella cell with dual-microdisk electrode," *Bioelectrochemistry* 54:33-37.

Ohno-Shosaku T, Okada Y (1985) "Electric pulse-induced fusion of mouse lymphoma cells: roles of divalent cations and membrane lipid domains," *J Membr Biol* 85:269-280.

Polla DL, Erdman AG, Robbins WP, Markus DT, Diaz-Diaz J, Rizq R, Nam Y, Brickner HT, Wang A, Krulevitch P (2000) "Microdevices in medicine," *Annu Rev Biomed Eng* 2:551-576.

Schwab ME (2002) "Repairing the injured spinal cord," *Science* 295:1029-1031.

Wang XB, Huang Y, Wang X, Becker FF, Gascoyne PR (1997) "Dielectrophoretic manipulation of cells with spiral electrodes," *Biophys J* 72:1887-1899.

Wang XB, Yang J, Huang Y, Vykoukal J, Becker FF, Gascoyne PR (2000) "Cell separation by dielectrophoretic field-flow-fractionation," *Anal Chem* 72:832-839.

* cited by examiner

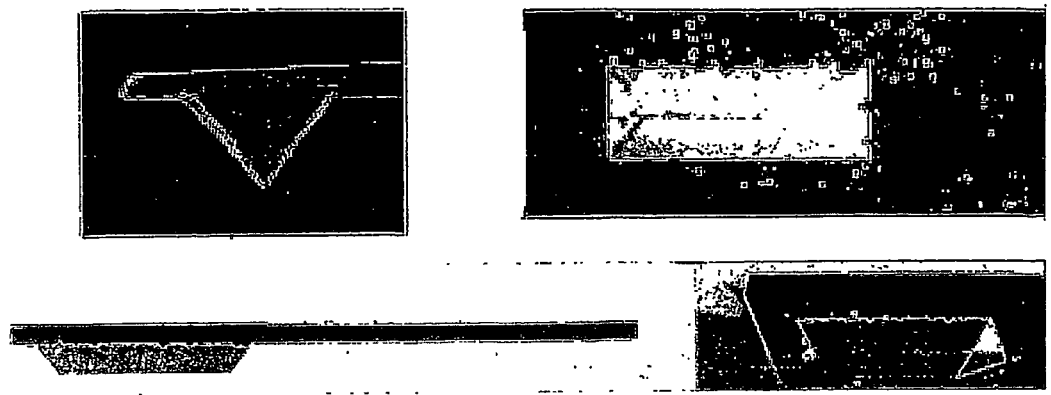
FIG. 3A-D
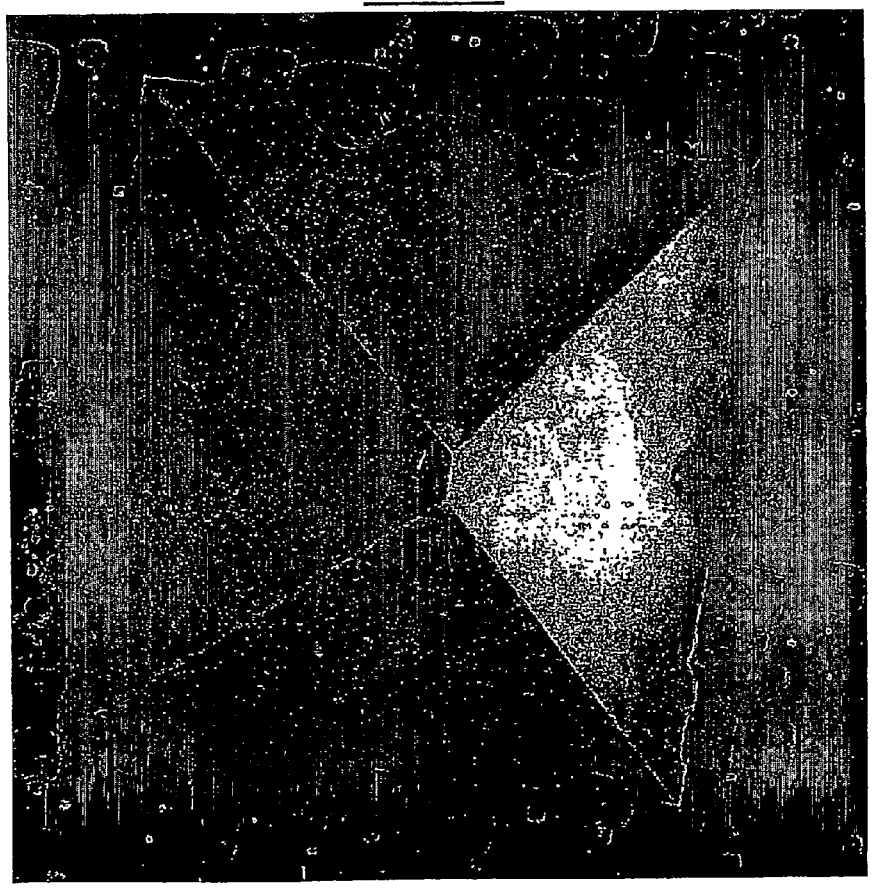
FIG. 3E

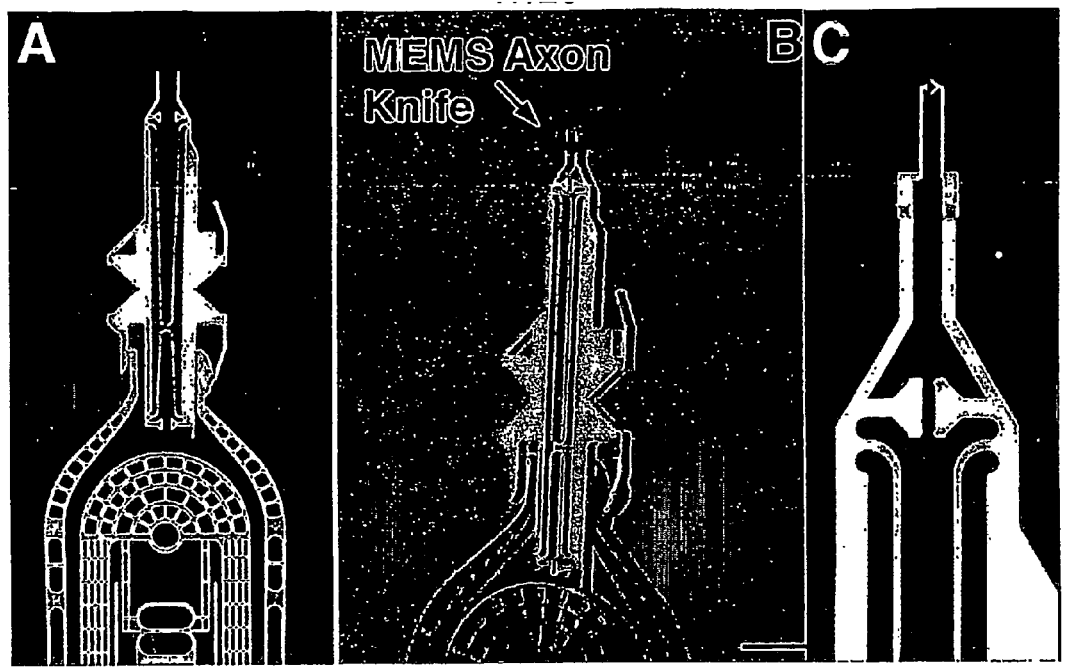
*FIG. 12*
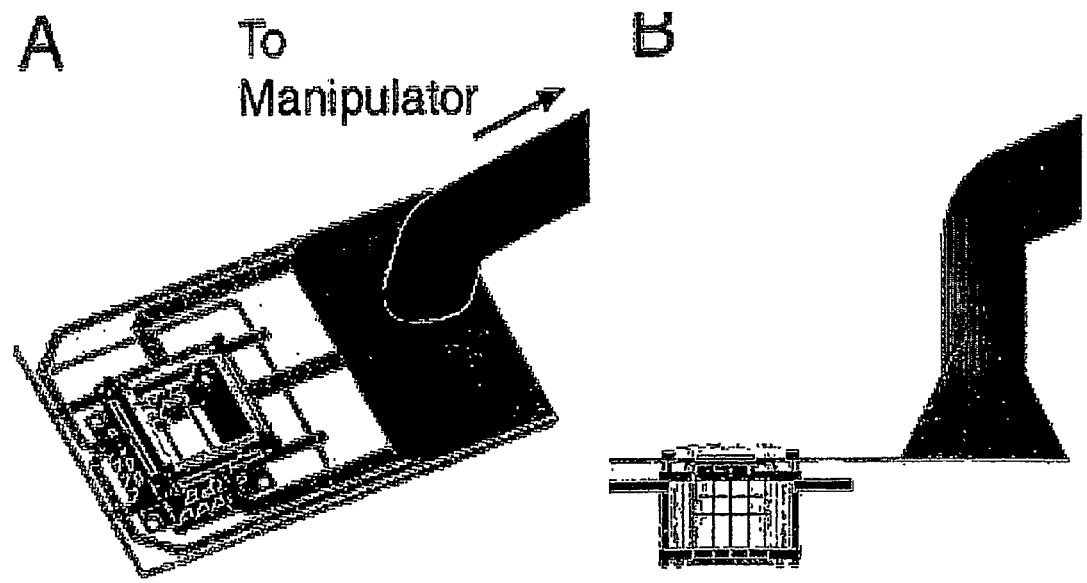
*FIG. 13A*            *FIG. 13B*

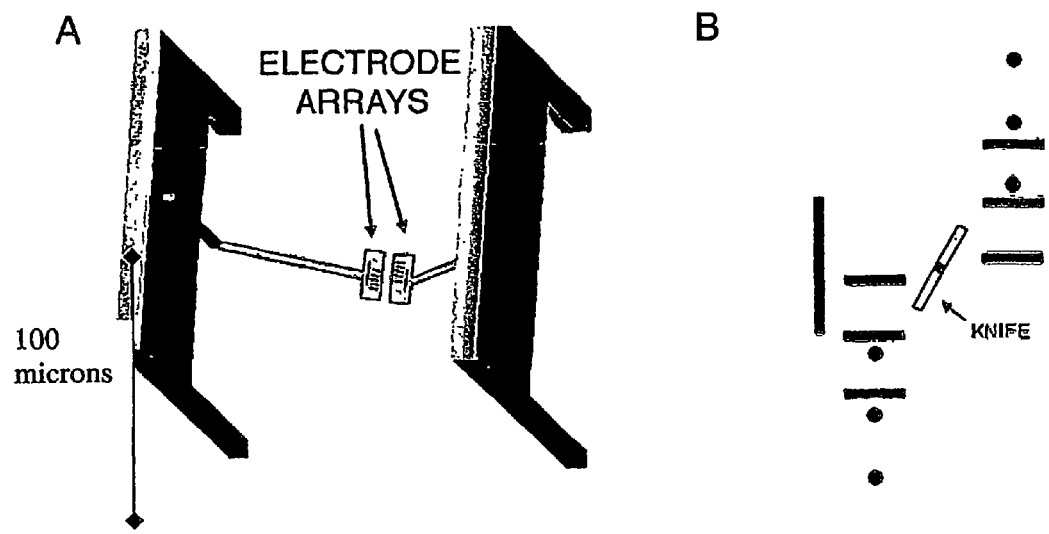
*FIG. 16A-B*
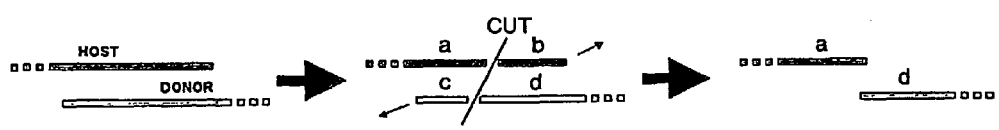
*FIG. 17*
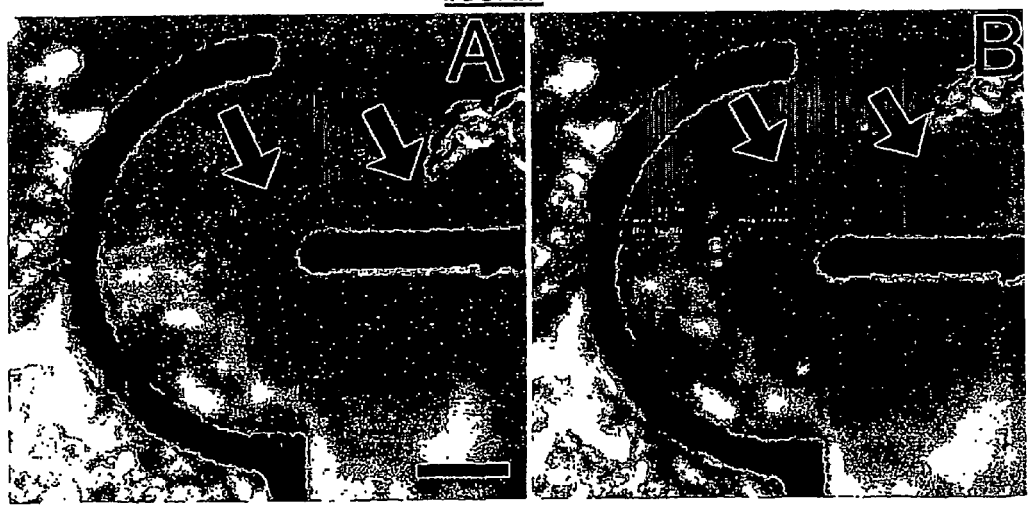
*FIG. 19A-B*

Opening for Microknife

A - Surgical frame
B - Nerve sealing gasket
C - Bottom plate of surgical frame
D - Host and donor axons to be fused and repaired
E - Inflow tubes
F - Outflow tubes
G - Wave guide
H - Assembled MEMS axon repair platform
I - Micromanipulator to position MEMS axon repair platform

NERVE REPAIR BY SELECTIVE SURGICAL REPAIR OF AXONS

CROSS REFERENCE TO RELATED APPLICATIONS

This application is a National Phase filing from PCT Patent PCT/US2004/033784 filed 12 Oct. 2004, which claims priority from provisional patent application 60/510,788 filed 11 Oct. 2003. This application is related to U.S. patent application Ser. No. 11/404,261 filed 11 Apr. 2006, now U.S. Pat. No. 7,895,885, entitled METHOD AND SYSTEM FOR NANOKNIFE AND MEMS PLATFORM. These applications and all publications mentioned therein and herein are hereby incorporated herein by reference.

COPYRIGHT NOTICE

Pursuant to 37 C.F.R. 1.71(e), Applicants note that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

The present invention relates to methods and/or systems and/or apparatuses for neural repair. The present invention also relates to methods and/or systems and/or apparatuses for constructing microfabricated systems. In further embodiments, the invention involves methods and/or systems and/or apparatuses allowing for controlled manipulating of very small structures, such as tissues, cells, portions of cells, microfabricated devices, other structures, etc. In further embodiments, the invention involves methods and/or systems and/or apparatuses for axon manipulation and axon repair.

BACKGROUND OF THE INVENTION

The discussion of any work, publications, sales, or activity anywhere in this submission, including in any documents submitted with this application, shall not be taken as an admission that any such work constitutes prior art The discussion of any activity, work, or publication herein is not an admission that such activity, work, or publication existed or was known in any particular jurisdiction.

Many fields of human endeavor, both biological and non-biological, would benefit from more precise manipulation of very small structures. Consider the nervous system. Injury may occur to the central nervous system (CNS), consisting of the eyes, brain, and spinal cord, or the peripheral nervous system (PNS), consisting of nerves to arms, legs and internal organs. In humans and other mammalian species, injuries to CNS axon pathways can have extremely severe consequences such as paraplegia or tetraplegia. Peripheral nerve injury can also lead to severe sensory motor disability for extended periods that often only result in partial recovery.

As one example of the need for very small scale manipulation, currently, there is no specific therapeutic treatment for nerve injuries in either the CNS or PNS. Conventional research strategies call for the regeneration of axons from the site of injury to reestablish contacts with post-synaptic targets and thereby obtain functional recovery. Despite much research effort, the complexities of the cellular and molecular mechanisms required for adult axon regeneration have proven to be significant impediments to this approach.

A number of patents and publications discuss various MEMS devices and manufacturing techniques thereby. Some of these are listed below. This list is not intended to suggest that any search has been performed and is not exhaustive. These patents and their incorporated documents are incorporated herein by reference to provide background information and for any other purposes.

| Patent | Title |
| --- | --- |
| U.S. Pat. No. 6,125,007 | Membrane seal secured to inner and outer oscillating bearing members for small angle oscillations within confined axial space |
| U.S. Pat. No. 6,106,751 | Method for Fabrication needles via conformal deposition in two-piece molds |
| U.S. Pat. No. 6,015,599 | High Vertical Aspect Ratio Thin Film Structures for immunological isolation of cell transplants |
| U.S. Pat. No. 5,948,255 | Microfabricated thin film particle filter and methods of making it |
| U.S. Pat. No. 5,893,974 | Microfabricated capsules for immunological isolation of cell transplants |
| U.S. Pat. No. 5,651,900 | Microfabricated particle filter |
| U.S. Pat. No. 5,416,657 | Seal for bearings in small angle oscillation applications |
| U.S. Pat. No. 5,645,684 | Multilayer high vertical aspect ratio thin film structures |

SUMMARY

In specific embodiments, the invention involves methods for axon repair using a donor axon portion to repair a portion of an axon that is damaged or severed. In other embodiments, the invention involves methods for nerve repair by joining axon segments, without using a donor portion. In other embodiments, the invention involves methods for therapeutically treating nerve injury in mammalian species using axon repair.

In other embodiments, the invention involves a system and/or method for a novel microdevice, at times herein referred to as a nanoknife or nanoknife structure. In some references and the above referenced patent application, this structure is also referred to as a microknife and the two terms should be considered equivalent unless the context dictates otherwise. According to specific embodiments of the invention, a nanoknife is a MEMS fabricated knife structure as described further herein with nano-scale edge curvature, or sharpness. A nanoknife structure in specific embodiments of the invention is fabricated using techniques related to those used for fabricating an atomic force microscope (AFM) tip and has in some respects a similar geometry. However, a nanoknife according to specific embodiments of the invention has been shown to be more effective for performing certain activities, such as cutting cell structures, such as axons. A nanoknife module according to further specific embodiments of the invention includes additional features, such as a self-leveling mechanism.

In further embodiments, a microdevice such as a nanoknife according to specific embodiments of the invention is fabricated from a transparent material. Viewing through the microdevice allows observation of the action of the device.

In further embodiments, the invention involves a system and/or method for constructing a 3-dimensional microsystem apparatus from interlocking parts and in specific embodiments using a modular design. Such designs allows for substantially three-dimensional structures to be constructed from essentially flat plane wafer fabrication techniques. A specific application of such a design is a microsurgery platform structure, which in specific embodiments can be used to hold components of an axon repair system and/or other micro scale systems.

In further embodiments, the invention involves a particular example micro-surgery platform and/or method for axon repair. Such a platform can be comprised of one or more of a nanoknife mounted on a knife carrier, optionally one or more actuators for moving the nanoknife, and optionally one or more effector electrode contacts for moving donor and receptor axon segments and for encouraging fusion between axon segments.

In further embodiments, the invention involves systems and/or methods employing a surgical frame used for positioning and manipulating a micro-surgery platform according to specific embodiments of the invention. In further embodiments, the invention involves systems and/or methods employing microfluidic channels for delivering reagents to enhance axon and nerve repair. In further embodiments, the invention involves systems and/or methods employing waveguides to enable optical monitoring, visualization, and/or the use of light sources to enhance axon and nerve repair.

In further embodiments, the invention involves systems and/or methods for manipulating small objects, such as tissues, cells and/or cell components such as axons, using electrical energy in a micro-system setting. In example embodiments, particular arrangements of electrodes and/or particular applications of electrical signals are used to effect precise movements and manipulations of micron scale objects in a micro-manipulation system. In further embodiments, a suspending medium for dielectrophoresis and electrofusion is developed and employed that is particularly suited for manipulating tissues, cells and/or cell structures such as axons.

In further embodiments, the invention involves a system and/or method of direct surgical repair of individual axons using an axon surgery platform fabricated by MEMS processing in order to effect therapeutic treatment of nerve injuries.

In specific examples, retinal axons are used for experimental tests because these axons have been well studied in their basic functions such as electrical conduction and axoplasmic transport, and methods for both short and long term retinal axon culture are available. Retinal axons are the functional neuronal unit in the optic nerve that relay visual information and are often damaged after injury or disease. Therefore, new treatment modalities that result in retinal axon repair are of practical clinical interest. Furthermore, since retinal axons share the same cellular make-up as other CNS and PNS axons, repair strategies demonstrated for retinal axons are expected to be applicable to axons in other parts of the nervous system. While retinal axon repair is an important embodiment of the present invention, the invention is not limited and has applications to the repair of other nerves, other regions of the nervous system, and to other operations on axons and other parts of neurons and other cells and/or portions of cells.

In specific embodiments, the invention involves a new nerve-repair paradigm in which the damaged region of individual axons is excised and replaced by healthy donor axon segments to reestablish neuronal connectivity and function. This proposed repair method involves the basic steps of axon cutting, manipulation by dielectrophoresis (DEP), and axon fusion.

In specific embodiments, the invention involves fabrication and use of a novel Micro Electromechanical Systems (MEMS) axon surgery platform to remove damaged axon segments and enable the splicing together of selected host and donor axons. This integrated MEMS microsurgical platform is assembled from individual micron-scaled modules that include a MEMS axon knife, and electrode arrays for DEP axon alignment as well as for electrofusion.

In further embodiments, the invention involves fabrication and use of a novel Micro Electromechanical Systems (MEMS) axon surgery platform that can cut and/or remove damaged axon segments and enable the splicing together of transected segments and/or host and donor axons. This multifunctional MEMS microsurgical platform is assembled from individual microfabricated modules that include a MEMS axon knife, and electrode arrays for DEP axon alignment as well as for electrofusion. An example device is roughly 1 cubic millimeter in size.

Other Features & Benefits

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents. Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. All references, publications, patents, and patent applications cited herein are hereby incorporated by reference in their entirety for all purposes.

BRIEF DESCRIPTION OF THE DRAWINGS

FIG. 3A-F illustrate scanning electron micrographs of an atomic force microscope (AFM) probe and three different views of different nanoknife designs according to specific embodiments of the invention.

FIG. 12 illustrates examples of thermal actuated microgrippers that can be used to assemble a platform of the invention, with (A) illustrating a Microgripper in the "open" position; (B) the same microgripper in the "closed" position holding a MEMS axon knife and (C) a second microgripper with different gripping ends.

FIG. 13A-C are diagrams illustrating an example design for a surgery platform, space frame, and carrier according to specific embodiments of the invention, showing (A) an oblique view of a surgery platform held in device carrier, with a handle provided to connect to a micromanipulator, (B) a side view, and (C) a higher magnification view showing a surgery platform held by carrier pins and rods.

FIG. 16 is a block diagram illustrating various aspects of an example electrode module according to specific embodiments of the invention and showing: (A) two-sets of three pairs of pin/probe-plate electrodes in an interdigitated pattern that can be selectively activated for DEP removal of axon segments; (B) example of combined electrode configurations on each electrode array.

FIG. 17 is a block diagram illustrating an example method for repair of axon segments by the cutting of host and donor axons and movement of unused axon segments according to specific embodiments of the invention.

FIG. 19A-C illustrate an example of axon movement in response to DEP fields (3 MHz, 10V amplitude, 10 mS/m) using a microfabricated electrodes according to specific embodiments of the invention, showing: (A) arrows pointing to axons before application of field; (B) axons moved towards top of panel in direction of curved plate electrode, in this example using a signal of 10Vp-p, 500 kHz; and (C) stimulus off. The scale bar indicates 20 microns.

DESCRIPTION OF SPECIFIC EMBODIMENTS

Figure 1:
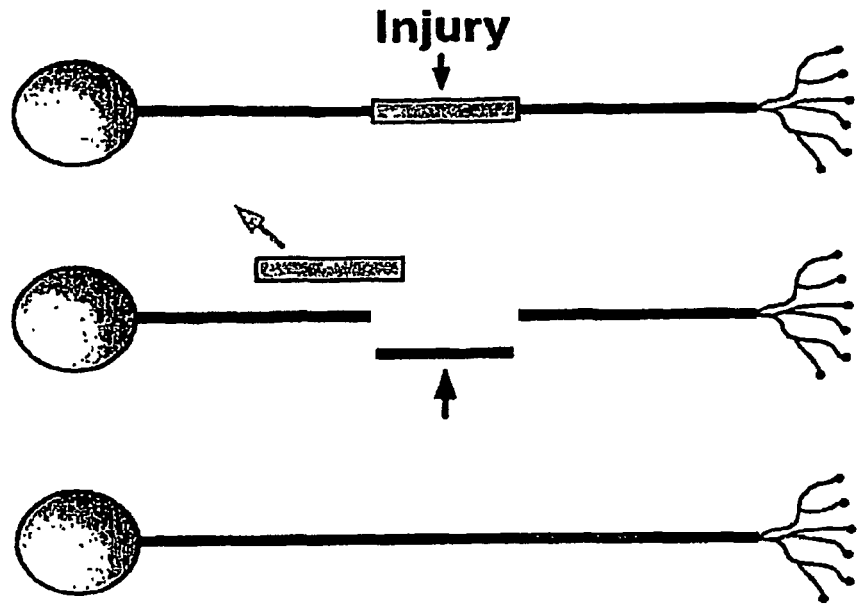
FIG. 1 is a block diagram illustrating a method according to specific embodiments of the invention for the surgical repair of damaged axons to achieve functional connection of nerves illustrating the steps of excision of the damaged axon region and the splicing in of a healthy segment from a donor axon.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

1. Nerve Repair Overview

One application of high interest for systems and methods of the present invention is nerve repair, specifically axon repair. A unique characteristic of nerve cells is their ability to communicate with each other over long distances. This communication is transmitted along the axon, which is a cellular process extended by neurons to form synapses with partner cells. Axons range from 0.3 to 25 microns in diameter and in the case of spinal cord motor neuron axons, can extend up to a meter in length. Axons have a lipid membrane bilayer, cytoplasm, organelles and a cytoskeleton made up largely of microtubules and neurofilaments.

Axons are grouped together to form nerve bundles or axon tracts. A PNS nerve is comprised of axons accompanied by Schwann cells and overlying connective tissue layers that provide physical support for the nerve. The layer immediately surrounding axons is called the endoneurium and typically encases a number of axons to form an axon fascicle. Groups of fascicles are in turn encased by additional connective tissue layers known as the perineurim and the epineurium. Thus PNS nerves can be viewed as connective tissue conduits containing axons. Axons serve as the basic unit for neurotransmission within the nervous system, and are the critical cellular component that is damaged after injury.

Axons in the CNS, including retinal axons in the optic nerve, are generally not associated with connective tissue layers. They are however ensheathed by oligodendrocytes that serve a similar myelination function as Schwann cells in the PNS. Axons that originate from the same CNS region run together as a "tract" within the brain or the spinal cord to innervate the appropriate targets. The positions of the major axon tracts in the CNS are well mapped. Unlike the spinal cord, the optic nerve is a unique part of the CNS in that it contains only axons of retinal ganglion cells with no other contaminating neuron or axon types. Isolated retinal tissue explants in culture gives rise to a pure population of retinal axons that are amenable for study. This relatively simple organization has made retinal axons and the optic nerve favorite systems for the study of CNS axon injury and regeneration.

Thus, according to specific embodiments of the invention, nerve repair is accomplished by selectively repairing one or more principal axons in a damaged nerve area. Because of the fact that adjacent axons carry similar neural information and the fact that the nervous system is capable of substantial plasticity it is not necessary in all cases to exactly match ends of a severed axon in order to restore meaningful motor and/or sensory functionality.

The most immediate effect of axon damage is the loss of action potential conduction. However, axon injury also triggers a cascade of irreversible cellular changes that affects the axon, its post-synaptic targets, and the neuron itself. For example, after PNS axon damage, the distal portion of the axon isolated from its cell body is degraded in a process called Wallerian degeneration. This process results in elimination of the axon terminal arborization and its synapses from the post-synaptic target. With the loss of the distal axon segment, the myelin sheaths of the degenerated axons are also removed. Wallerian degeneration in turn triggers changes in the target cell due to the lack of synaptic innervation. For example, cells in the visual centers of the thalamus are known to atrophy following damage to the optic nerve.

The other major consequence of axon damage is the eventual loss of the original neuron itself. Neurons with severed axons are known to undergo apoptotic cell death, presumably due to the lack of trophic factors normally derived from the target cell and retrogradely transported back to the neuron. This process has been well studied in the visual system where RGCs whose axons are severed by optic nerve injury begin to die after a few days, and only 10-20% of RGC remain after two weeks.

Regeneration in the PNS and CNS

Conventional teaching states that injured PNS axons can successfully regenerate and re-connect with their targets. PNS axons that are injured but remain confined within their endoneurial sheaths, can indeed sprout a new growth cone and grow back to their post-synaptic partners. In actual clinical situations however, peripheral nerve damage often disrupts the connective tissue layers in the nerve, so that axons are not able to track and regenerate within their original endoneurial sheaths. The growth of regenerating axons in the PNS is also quite slow at 1-2 mm/day and often require up to 1-2 years to grow back to their target cells after severe injury. During this extended period, neurons can die from the lack of retrograde trophic support and dennervated target tissues such as muscles can atrophy. All of these factors lead to the fact that full recovery after significant peripheral nerve injury is the exception rather than the rule.

Unlike axons in the PNS, there is no meaningful regeneration of injured axons in the CNS; thus optic nerve injury results in permanent blindness, and spinal cord transection results in tetraplegia or paraplegia. Research has demonstrated that this lack of CNS axon regeneration is likely due to inhibitory proteins expressed in adult CNS myelin. In addition, there is also emerging evidence that adult neurons such as Retinal Ganglion Cells shut off their axon growth program soon after birth, and are thus intrinsically less able to regrow after injury. In sum, neurons do not have sufficient ability to fully regenerate and re-establish functional connections after either PNS or CNS nerve injury.

Autologous nerve grafts are sometimes performed after peripheral nerve injury in an attempt to bridge a gap in the injured nerve and provide a tissue conduit to promote PNS axon regeneration. Donor nerves can be obtained from a number of sites. During grafting, the severed ends of two nerves are brought together and a surgical anastomosis is performed using sutures. It is important to note that in nerve grafting, the donor nerve is used only as a connective tissue conduit, and axons within the graft are unused and left to degenerate. The success of PNS nerve grafting depends solely on axon regeneration and is dictated by how many injured axons find their way into endoneurial sheaths. At present, clinical management of CNS and PNS nerve injuries does not directly address repair at the level of individual axons. As a result, injuries to CNS axons and serious peripheral nerve injuries generally lead to disappointing outcomes involving significant functional disability.

The core strategy currently pursued for improved nerve damage treatment is the promotion of axon regeneration. Several approaches are being investigated. In the optic nerve, these include the identification of myelin proteins that inhibit retinal axon regeneration and the development of pharmacologic means to suppress their inhibitory activity. Another approach examines the molecular mechanisms underlying retinal axon guidance during embryonic brain development, with the hope that these axon guidance mechanisms can be harnessed to promote regeneration of injured retinal axons in the adult. As a group, these approaches have in common the aim to promote the re-growth of injured axons and thereby re-establish neural circuits to achieve functional recovery. However, axon regeneration as a therapeutic strategy has not met with much success thus far. Not only must axons be coaxed to grow over long distances, this growth must also be controlled so that regenerating axons are able to find their way back correctly to the appropriate target tissues. Axon regeneration along incorrect pathways must be minimized to prevent formation of abnormal neuronal circuitry. The series of secondary cellular changes that occur after axon damage brings about other challenges. For example, a regenerating axon must re-establish a highly specific pattern of axon arborization and synaptic contacts with the post-synaptic target cell. In addition, with prolonged dennervation, postsynaptic targets themselves may atrophy and become incapable of receiving input. Finally, while waiting for axon regeneration, the neurons themselves must be supported and prevented from undergoing retrograde neuronal death.

One feature of any therapeutic treatment for axon damage is that it should be implemented before the onset of Wallerian degeneration and the secondary effects on post-synaptic cells and neuronal survival. In the PNS, the time window between injury and onset of axonal changes has been reported to be 24-48 hrs. In the CNS, Wallerian degeneration occurs more slowly or to a lesser extent after axon damage and the time interval after injury available for intervention to conduct axonal repair is longer. Nevertheless, in both the PNS and CNS, axon regeneration, if it can be coaxed to occur, is much too slow to prevent the loss of synaptic input, post-synaptic cell atrophy, and neuronal death.

2. Nerve Repair by Repair Of Individual Axons

According to specific embodiments of the invention, a method for neural repair involves direct repair of individual axons. One method according to specific embodiments of the invention is illustrated in FIG. 1. An example method begins with the excision of the damaged axon region. A donor axon segment is then brought into the gap within the host axon. Once aligned, the host and donor axon segments are then fused to establish functional integrity. Compared to strategies based on axon regeneration, surgical repair according to specific embodiments of the invention can occur soon after injury and thus minimize or eliminate the secondary degenerative effects on neuronal circuitry, that once initiated, are difficult to reverse.

The manipulation of axons that are only one to a few microns in diameter is not feasible using current surgical tools and techniques. Thus, in further embodiments, the invention provides for the design, fabrication, and use of a novel MEMS axon surgical platform that enables the precise manipulation of axons at the length scale of microns. By exploiting MEMS microtechnology, electrokinetic methods for axon manipulation, and fundamental principles of neurobiology, the invention allows the human surgeon to engage in direct axon repair at a cellular level.

Examples of Axon Cutting, Alignment, And Fusion

Figure 2:
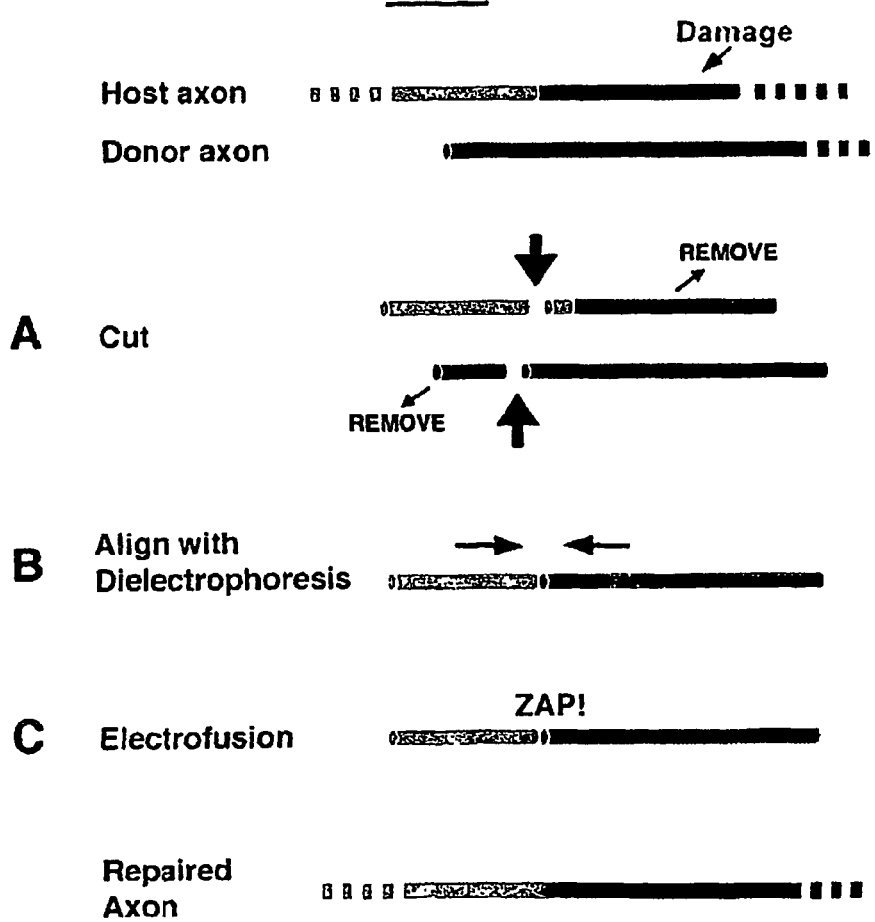
FIG. 2 is a block diagram illustrating MEMS assisted axon repair according to specific embodiments of the invention (in this figure, dotted patterns represent continuation of the axon segments).

The basic steps for fusing a host axon segment with a donor segment according to specific embodiments of the invention are shown in FIG. 2. After the introduction of a donor axon, the first step uses a nanoknife to cut the donor axon to the correct length and to trim back the host axon to remove the damaged region (FIG. 2A). The second step is the alignment of the ends of the host and donor axons, for example using dielectrophoresis (DEP) (FIG. 2B). According to specific embodiments of the invention, this is performed by a MEMS DEP electrode array, examples of which are described herein, configured to deliver optimal dielectrophoretic forces to axons.

Once aligned and with the axons in close apposition, a cell fusion enhancer (e.g., electrofusion) can be used to splice together the two ends (FIG. 2C). When performing nerve repair using donor axons, these same steps of MEMS assisted axon fusion are then repeated at the other host axon and donor axon junction. According to this method of axon repair, the final result is the substitution of the damaged segment with a healthy segment and the re-establishment of axon continuity.

According to specific embodiments of the invention, the individual steps described above are performed by MEMS microdevices, such as a nanoknife and optional supporting structures as described further herein.

In alternative embodiments, and in some situations, axons may be repaired without use of a donor segment and with or without cutting the damaged regions of axons, but using one or more of the methods and/or devices described herein to position axon ends and encourage fusion.

3. An Example MEMS Microsurgery Platform

In further embodiments, the invention is involved with an example MEMS designed microsurgery platform that can be effectively used in micro manipulation tasks, such as to perform the steps described above. Discussed below are several detailed examples of MEMS-based surgery platforms and devices and techniques for building the same. It is believed that each of these devices and techniques is novel and has applications other than to the nerve repair methods of the invention. Also, these specific platforms are provided as examples only, and the methods of the invention may be performed using other devices and/or systems and/or methods than any of the specific examples provided herein.

MEMS has its roots in the semiconductor industry in which the basic steps of lithography, chemical etching, and silicon doping are used in the manufacturing of integrated circuits. These processing methods have previously been adopted and shown able to create a wide range of micron-sized devices using silicon's or some other fabrication substrate's mechanical properties. With the addition of sensing and actuation mechanisms as well as electronic controls, MEMS microdevices are capable of carrying out useful function on a micron-scale level.

In specific embodiments, the present invention involves the repair of damaged axons using MEMS assisted axon surgery and specifically, cutting, alignment, and fusion of axons using a MEMS axon surgery platform. This MEMS platform goes beyond the limitations imposed by planar processing and presents an efficient 3D configuration to deliver one or more functions to achieve axon repair using novel MEMS fabricated component devices.

According to specific embodiments of the invention, MEMS assisted axon repair begins with the trimming of the ends of both the host and donor axon segments for alignment and fusion. According to specific embodiments of the invention, a device for axon cutting meets a number of criteria. These include precise cutting at a specific location, the production of clean cuts, repeatability, and minimal dislocation of the axon segments after cutting. At the present time, a preferred embodiment includes a novel Nanoknife, as described further below. Such a knife can in some embodiments be mounted into a self-compliant frame and can be further integrated into a MEMS device for performing one or more steps of an axon repair method according to specific embodiments of the invention.

Other methods for cutting biological tissues can also be used for axon repair according to specific embodiments of the invention, such as laser thermal ablation. This approach has been integrated into standard optical microscopes and used for cellular dissection (Berns et al., 1998). Thermal ablation however can result in significant damage to cellular proteins and organelles near the ablation site, and requires substantial operator experience and skill, thus this is presently not a preferred method. Less destructive non-thermal laser ablation may be achieved using a picosecond laser, or by using a Nd/YAG laser to deliver a shock wave to physically disrupt cells (Sims et al., 1998). Performing an axon repair method as described herein using other cutting methods will be readily understood to those familiar with those arts, the presently preferred method involves a nanoknife as discussed further below.

4. A Nanoknife for MEMS Surgery and Other Uses

Thus, according to specific embodiments, the present invention involves a novel nanoknife design. Nanoknives according to specific embodiments of the invention can be fabricated from a number of different materials and in a number of different configuration. While an initial area of interest for using such nanoknives has been in axon repair and other microsurgery as described herein, other uses for such devices have been contemplated since the time of conception of the device and have been further investigated and described herein.

A nanoknife according to specific embodiments of the invention can be fabricated in a number of ways. In one example fabrication scheme, silicon etching techniques, as used to manufacture atomic force microscopy (AFM) probes, are used in nanoknife fabrication. AFM probes are typically made by depositing a layer of silicon nitride into a pyramidal pit mold etched in a silicon wafer; the mold is then dissolved, leaving a strong self-supporting thin film structure of silicon nitride that forms a single atomically sharp point.

A knife design according to specific embodiments of the invention uses an analogous technique, elongating the point into an atomically sharp edge. Silicon nitride is one material used in specific embodiments and is a covalently bonded ceramic not subject to plastic deformation at room temperature. The force required to cut an axon is too small to damage the nanoknife blade, and knives made with silicon nitride readily hold their sharp edge. With the knife mounted on a compliant suspension according to specific embodiments of the invention, the nanoknife can be more repeatedly used without damage as the compliant suspension limits the applied force to the correct range.

In further specific embodiments, a nanoknife according to specific embodiments of the invention is fabricated in such a way as to be transparent through the knife and through the blade. Thus, the invention provides a mechanism to see axons or other materials being cut or manipulated through the knife and verify axon position prior to cutting. Silicon nitride knives can be made to high tolerances and can be readily incorporated into the design of a MEMS axon surgery platform according to specific embodiments of the invention as described herein.

Other materials can be used to form a nanoknife blade according to specific embodiments as discussed below. In some applications, one or more of these other materials may be a preferred embodiment. In some embodiments, these other materials are either transparent, or deposited in a thin enough layer to be transparent. For fabricating a nanoknife using a mold according to specific embodiments of the invention, any material that can conformably line a mold cavity by means of low pressure chemical vapor deposition (LPCVD) or plasma deposition could be used. Examples of such materials include: nitride (e.g., low stress silicon rich silicon nitride); amorphous silicon; silicon carbide; diamond; amorphous carbon; etc., as well as any combination of such materials and any suitable ceramic or metal or mineral or crystalline or plastic material.

In further embodiments, any material that can line or fill a mold by thermal melting can be used. Preferably, the material will be one that can be made to wet the mold so it gets pulled in to the sharp corners. Such materials include various glass material suitable for MEMS fabrication (e.g., IP 900 vwg from Ferro Corp.).

In further embodiments, any material that can form a sharp edge by mechanical cleaving can be used. Examples of such materials include obsidian.

In one currently preferred embodiment, low stress silicon nitride that is deposited by low pressure chemical vapor deposition (LPCVD) at about 835° C. with excess silicon (not stochiometric $Si_3N_4$, which has a high tensile stress) is used in a current embodiment of the knife.

In an alternative embodiment, amorphous silicon can be deposited to line a nanoknife mold, for example by LPCVD at about 500° C. Similarly, silicon carbide can be deposited by LPCVD.

Alternatively, materials such as diamond can be grown on silicon and thus can be grown in a nanoknife mold according to specific embodiments of the invention. Alternatively, materials such as amorphous carbon can be deposited in a mold by sputtering.

Alternatively, various glass materials can be deposited into a mold to form a nanoknife or used as part of a nanoknife structure. For example, glass frit can be melted at about 900° to 1,000° C. to make a solid knife. Glass can also be used in some embodiments to strength a nanoknife. For example, in applications where a stronger knife is desired, a nitride (or other material) membrane knife line a nanoknife mold as described herein can be filled with glass.

Obsidian and possibly some other materials can be mechanically cleaved or chipped to form an atomically sharp edge. To make a usable device, the edge can be embedded in wax to hold it so that the chip can be sawed or ground to produce the geometry and dimensions needed to be mounted on the knife suspension. After the obsidian block has been cut to the desired length, width, and height, the wax can be melted, the knife cleaned in solvent, and then glued onto the suspension.

AFM Probe-Based Nanoknife

Figure 3F:
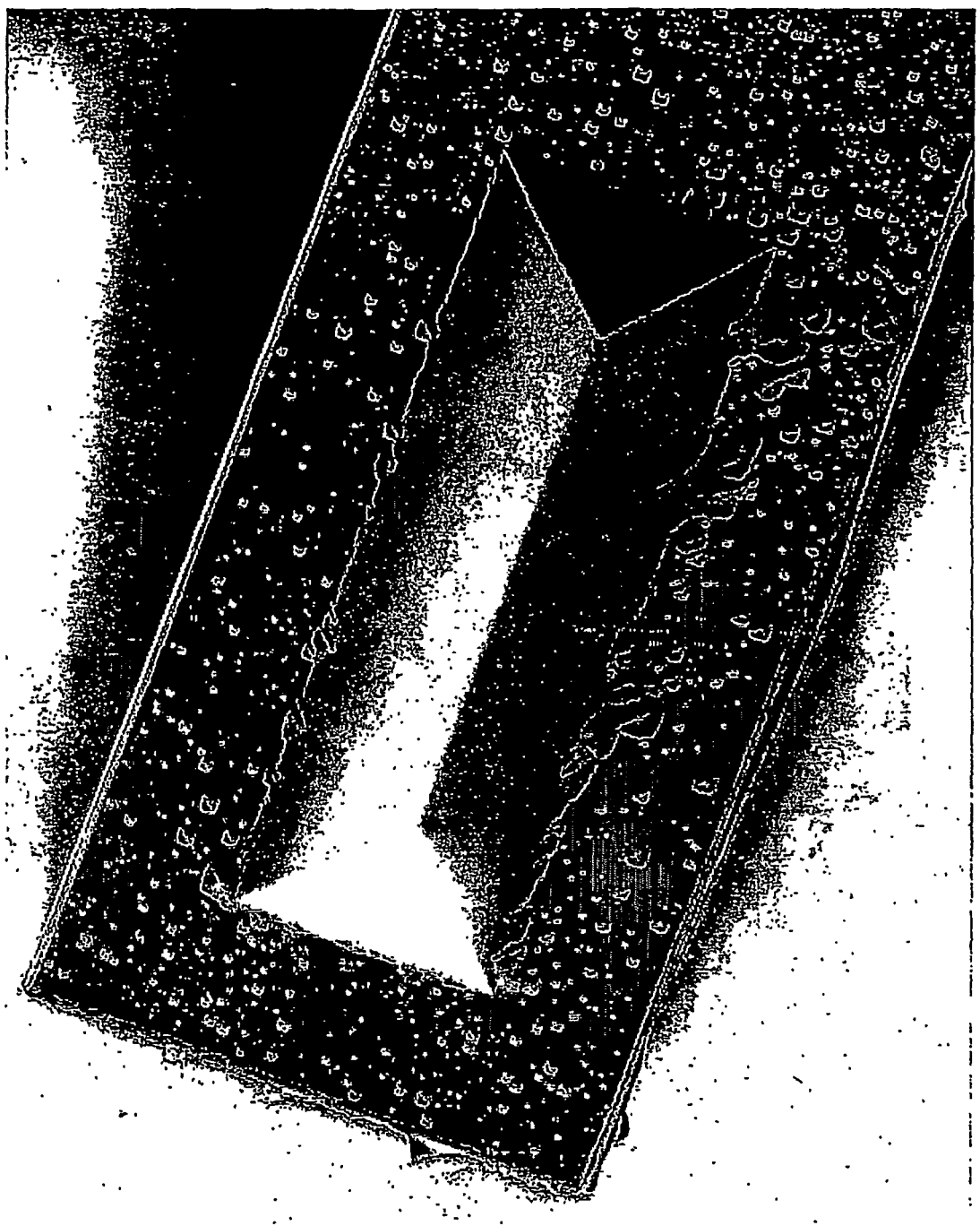

A typical AFM pyramidal shaped tip is shown in FIG. 3A. According to specific embodiments of the invention, a nanoknife is fabricated from silicon nitride in a similar manner to an AFM tip, but where the pyramidal tip is extended in one dimension to form a near-atomically sharp edge ranging in length from about 3 microns to about 200 microns, or larger or smaller depending on the intended application. The cantilever portion of the knives can be used for attachment to a micromanipulator for positional control. As an example, nanoknives with edges 10 microns in length were used to cut single mouse retinal axons in culture, which typically are 1 microns in diameter. The 200 microns knives were used in experiments to simultaneously cut 2 or more axons. FIG. 3A-F illustrate scanning electron micrographs of an atomic force microscope (AFM) probe and three different views of different nanoknife designs according to specific embodiments of the invention FIG. 3B shows a top view of prototype MEMS axon knife with a 100 microns cutting edge; FIG. 3C shows a side view; and FIG. 3D an oblique view. FIG. 3E is a micrograph showing a nanoknife having a shorter cutting edge and FIG. 3F is a more detailed micrograph showing a nanoknife having a more elongated cutting edge.

In further embodiments, a MEMS nanoknife itself is a pyramid-like structure, converging to a sharp cutting edge along its zenith. In specific embodiments, this structure is formed by conformally depositing a thin layer of amorphous material over a mold etched into silicon by anisotropic etching, for example using aqueous potassium hydroxide (KOH)

or other suitable etch materials. In specific embodiments, it will be understood that the selection of etch material will be in part influenced by the selection of material for the nanolanife mold. This solution reacts with silicon but etches very slowly along the <111> crystal orientation: the rate of etching in other directions is at least 400 times faster than along the <111> direction. Etching with KOH solution in single crystal silicon produces specific shapes and patterns beneficial for various MEMS applications, including the nanoknife.

Thus, according to specific embodiments of the invention, to fabricate the knife mold, a substrate of single crystal silicon, with a flat, polished surface oriented in the <100> direction is lithographically patterned on top with exposed windows representing the desired shape and size of the final base of the knife pyramid. KOH etching into these windows produces a pyramidal pit with obliquely angled and ultra-smooth sidewalls. As the etch progresses and the pit grows deeper, the angled sidewalls eventually converge in the middle forming ultra-sharp, V-shaped groove. KOH etching is so precise that the V-shaped groove converges to a nearly molecularly thin line at the trough, permitting the formation of an ultra-sharp knife edge upon molding.

Control of Knife Geometry

The length of this sharp groove, which corresponds to the length of the molded knife edge, is generally influenced by the size and shape of the original lithographically patterned window and the duration of KOH etch. For example, with a rectangular etch window, a higher aspect ratio (e.g. elongated rectangle) produces a longer groove and thus a longer knife edge when molded. Shorter etch times-though long enough for the lengthwise sidewalls to converge—also tend to produce lengthier grooves and thus longer knife edges. Conversely, starting with a square etch window (lowest aspect ratio) eventually results in sidewalls converging to a sharp point, with no edge length. Thus, simultaneous control of the overall shape of the pyramid base, the height of the pyramid, and the length of the cutting edge is preferably achieved by coordinating the size and shape of the original etch window with the duration of the etch itself.

Lubrication of Cutting Edge

According to further specific embodiments of the invention, to prevent debris from cells and/or membranes or other materials from sticking to the knife surface (e.g., silicon nitride or any of other materials suitable for fabricating a nanoknife, such as those discussed herein), a lubrication method or substance is applied. Various liquid, gel, or solid materials can be used according to specific embodiments of the invention, so long as they have the property of reducing unwanted friction between the knife edge and/or body and the particular application to which the knife is put. Furthermore, different particular solutions will be desirable for different applications.

As examples, two specific methods of knife lubrication have been investigated; other methods will be understood from these teachings. In one approach, a droplet of a liquid or near liquid gel, such as perfluoropolyether, is placed on the knife. The hydrophobicity of this fluid along with surface tension at the lubricant-water interface ensures that approximately only a molecularly thin layer forms at the apex of the knife, along the cutting edge. This mobile lubricant method has been tested experimentally and was effective in preventing adhesion of debris with the knife.

A second approach uses a 3% (weight/volume) of bovine serum albumin (BSA) in phosphate buffer saline. This can be done in lieu of or in addition to the lubricant in specific applications. A droplet of the BSA solution is applied to the knife and incubated for 10 minutes at room temperature prior to usage. This approach likewise has been demonstrated to mitigate sticking, since cut materials generally do not adhere to the knife after cutting, and the knife tends not to accumulate debris after repeated uses.

In a further, more specific example, a small droplet of lubricant is placed near the base of the knife by micropipette, or by pin transfer. The bulk of the liquid will form a meniscus around the knife and act as a reservoir that maintains a thin film of lubricant over the knife by surface diffusion. The thickness of the film at the knife edge is generally on the order of 1 or 2 monolayers, because the surface tension forces are acting to pull all bulk liquid away from that edge. If the lubricant is wiped off the edge, it is rapidly replaced by surface diffusion from the reservoir. In particular embodiments, the size of the reservoir can be increased by etching a cavity in the suspension to hold more liquid. This can also protect the reservoir from mechanical wiping in use. A number of different lubricating materials can be used in such an embodiment, e.g. Perfluoropolyethers, other hydrophobic materials, hydrophilic materials, etc.

In alternative embodiments, as in the lubrication of magnetic recording disks, a monolayer of lubricant can be bonded to the surface of the nanoknife, for example by heating. A bonded lubricant according to specific embodiments of the invention can be used either instead of or in addition to a lubricant from a reservoir.

A commonly used lubricant is zdol. Zdol is a perfluoropolyether having an OH containing group at each end, e.g.,:

$X—CF_2—O—(CF_2—CF_2—O)_p—(CF_2O)_q—CF_2—X$.

Experiments were done with Fomblin Y LVAC 14/6 perfluoropolyether vacuum pump oil which has an average molecular weight of 2,500 and a viscosity at 20 C of 140 cSt. The formula is: $CF_3O[—CF(CF_3)CF_2O—]_x(CF_2O—)_yCF_3$. A bonded layer on amorphous silicon can be formed using 1-octadecene by the method of Ashurst et. al. (for example, see stiction.cchem.berkeley.edu/alkene.pdf). In this case the mobile lubricant reservoir can be a hydrocarbon or a fluorocarbon.

Delivering Materials Precisely Using a Nanoknife

Figure 4A:
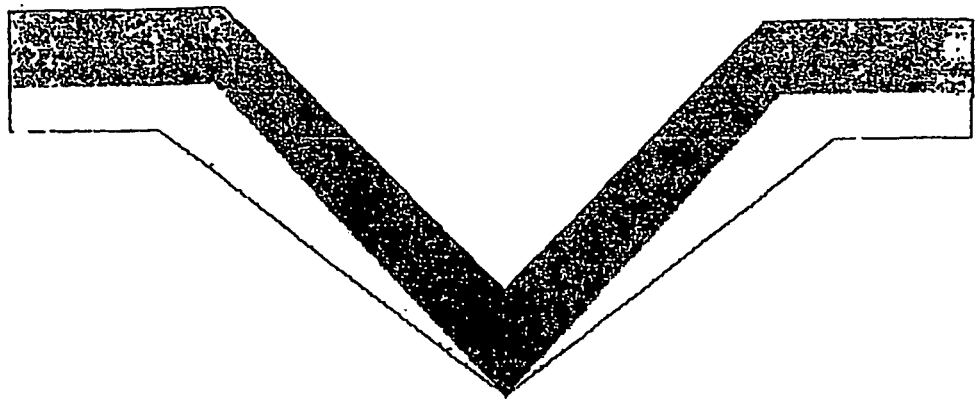
FIG. 4A-B are block diagrams illustrating examples of a nanoknife design according to specific embodiments of the invention: (A) shows a knife with lubricant; (B) alternatively shows a layer of reagent under the lubricant and further indicates dissolution, diffusion, crystallization as material from a reservoir (D) is deposited at an edge (E) according to specific embodiments of the invention.
Figure 4B:
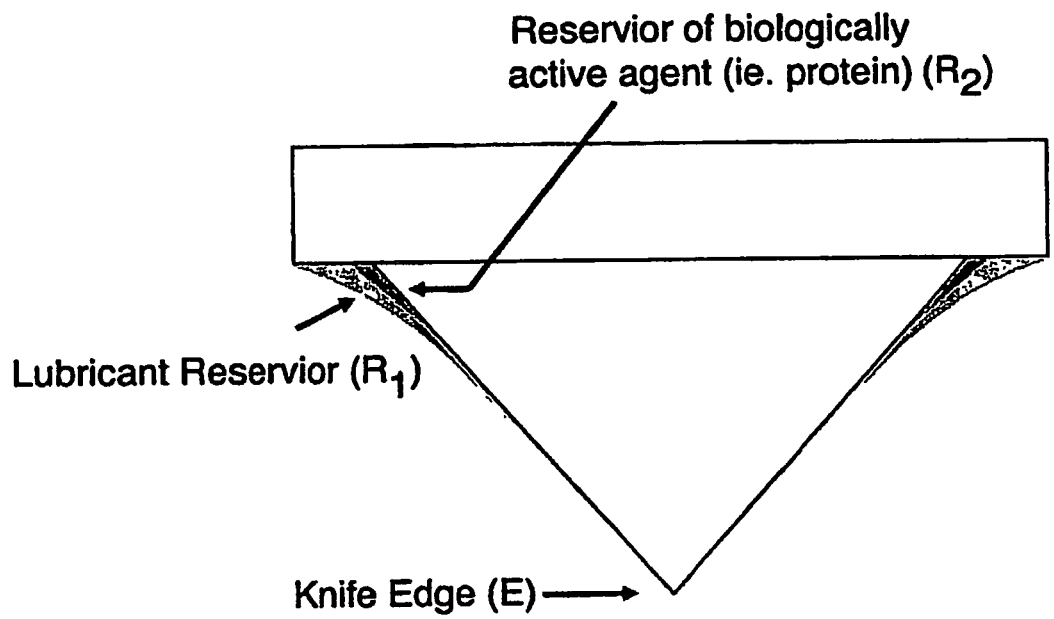

Biologically active agents (e.g. proteins, oligonucleotides, macromolecules, etc.) or any other desired substance, can be dissolved in the lubricant and applied to the knife. If the solubility of the reagent in the lube is low, reagents can be maintained for delivery by having its own reservoir deposited first under the lube reservoir (bottom figure). Features fabricated as part of the knife may also serve as reservoirs. FIG. 4A-B illustrate examples of a nanoknife design according to specific embodiments of the invention. In the example shown in FIG. 4B, equilibrium distribution of biologically active agent is maintained until $R_2$ is totally exhausted.

Thus, a nanoknife, with its nanometer sized edge and micron-sized length can serve as a very precise tool in depositing chemicals, macromolecules, other reagents onto precise locations on a cell or tissue. For example, a nanoknife can be used simply as a means to deposit labeled fluorescent molecules onto a specific population of cells, or to tag cells that have been selected by other means. It is particularly amenable for this purpose in BioMEMS devices. In addition, a nanoknife can also deposit tracer molecules in specific regions of cells or axons in order to experimentally monitor the flow of these molecules in relationship to the cell membrane under a variety of experimental perturbations. A similar method may be used to precisely deliver proteins, other biomolecules or pharmacological agents in the settings of basic research or as part of drug discovery processes.

Example Cutting of Cell Portions with a Nanoknife

Figure 5:
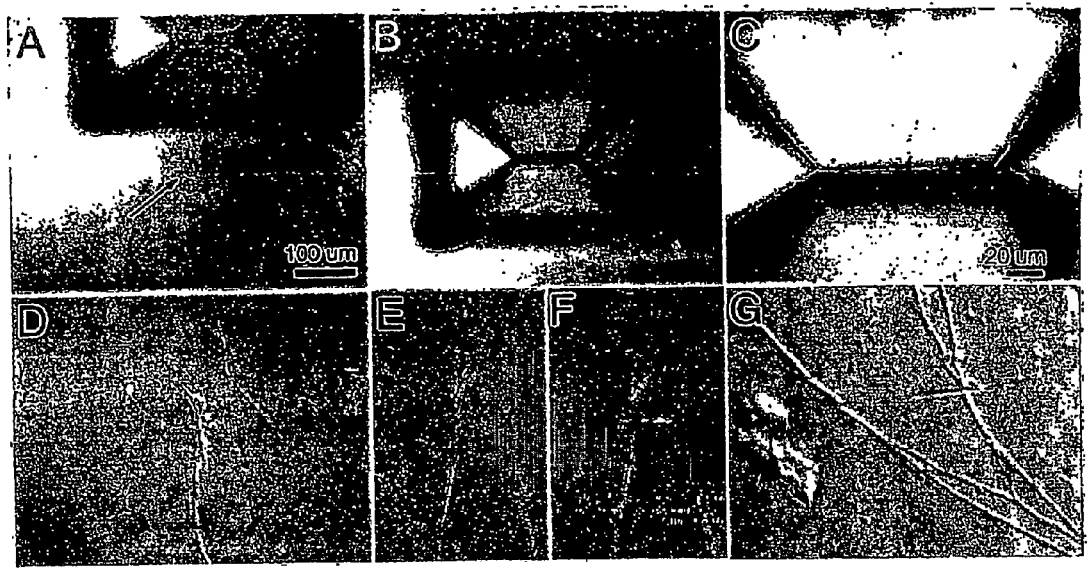
FIG. 5A-G show axons being cut using a nanoknife viewed from above and through the microdevice according to specific embodiments of the invention.

In experimental work, axons were grown from mouse retinal tissue explants cultured overnight on laminin-coated glass coverslip dishes. Axons were identified and positioned in the center of the field (arrow, FIG. 5A). Using a micromanipulator, a nanoknife was brought directly over the axon to be cut (FIG. 5B). The knife was lowered to cut the axon and then removed from the field of view (FIG. 5C, D). Cuts were quite apparent and sometimes resulted in the slight displacement of the cut ends from each other (FIG. 5D-F). MEMS knives with 100-200 microns long cutting edges were successful in simultaneously cutting two axons (FIG. 5G). Experimental results using a probe-like design according to specific embodiments of the invention indicated the importance of proper alignment of the long axis of the MEMS knife edge with the plane against which the knife was pressed (e.g., in vitro, a culture dish). In the figures, the scale bar in a is 100 microns and applies for both a and b. The scale bar in c is 20 microns and applies for c to g.

Furthermore, MEMS nanoknives according to specific embodiments of the invention have repeatedly made reliable cuts of individual living dendrites (1 microns diameter), axons (1-2 microns) in culture, unmyelinated axons (<2 microns diameter), as well as myelinated axons (5-10 microns diameter) obtained from adult animal nervous tissue. The nanoknives remained robust under repeated use (over 100 cuts in one case) without diminished performance or visible degradation of the knife surface or the suspension and frame.

Figure 6:
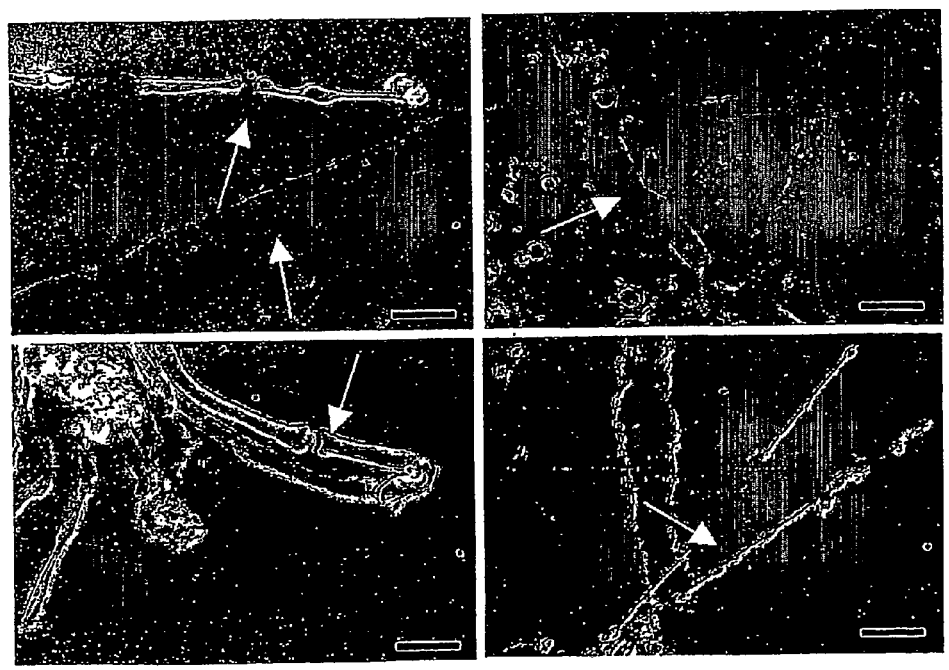
FIG. 6 illustrates examples of axons from adult nervous tissues cut with a nanoknife according to the invention, showing an example of sciatic nerve (left top and bottom) and optic nerve (right top and bottom), wherein axons have been cut at the position indicated by the white arrows.
Figure 7:
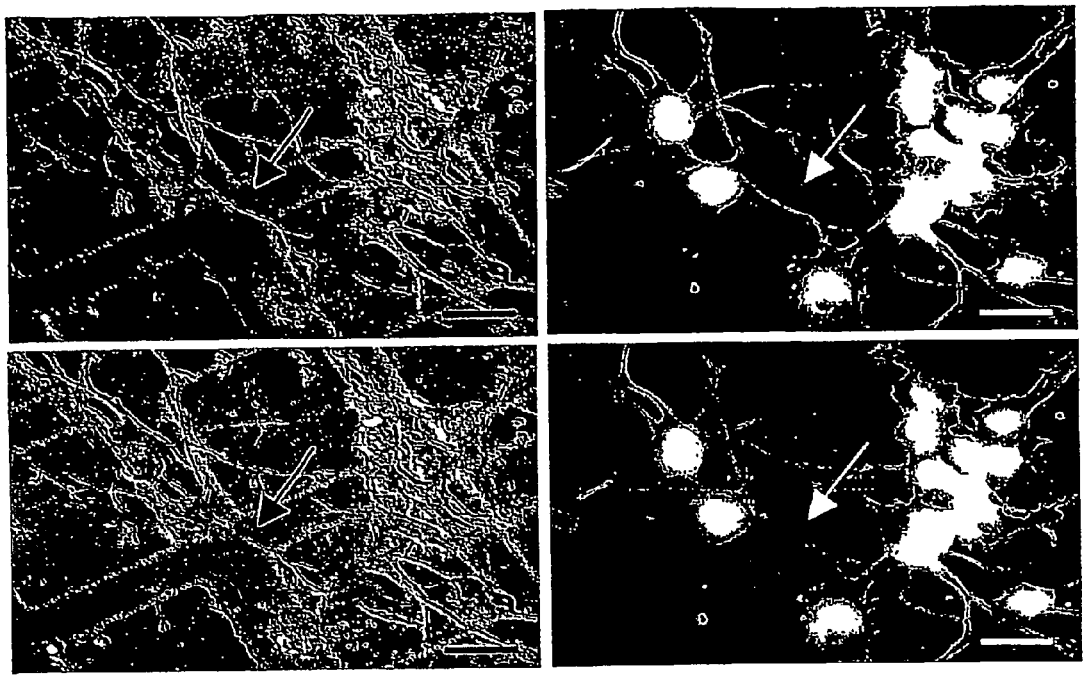
FIG. 7 illustrates examples of dendrites of hippocampal neurons at top before cutting and bottom after cutting with a nanoknife according to specific embodiments of the invention, showing brightfield images of neurons with dendrites to the left, and fluorescence image of the same neurons to the right, where these neurons are from a transgenic animal in which the neurons express green fluorescent protein.

In an example cutting process, a knife-and-suspension assembly as described below was held in a micromanipulator and viewed under a microscope, while the knife edge was positioned precisely over a desired target (e.g., an axon or dendrite). FIG. 6 illustrates examples of axons from adult nervous tissues cut with a nanoknife according to the invention, showing an example of sciatic nerve (left top and bottom) and optic nerve (right top and bottom), wherein axons have been cut at the position indicated by the white arrows. FIG. 7 illustrates examples of dendrites of hippocampal neurons at top before cutting and bottom after cutting with a nanoknife according to specific embodiments of the invention, showing brightfield images of neurons with dendrites to the left, and fluorescence image of the same neurons to the right, where these neurons are from a transgenic animal in which the neurons express green fluorescent protein. To actuate the cutting stroke, the knife was lowered edge-first via the micromanipulator onto the target until the knife edge touched the underlying substrate. Following the cut, the knife was raised and subsequently moved away from the target. Through the thin silicon nitride membrane of the knife, the target selection, local knife positioning, the cutting stroke as well as the actual contact between knife and target can be continuously monitored optically through the microscope. A mechanical load on the order of approximately 80 micro-N/ microns along the edge of the knife has been sufficient to produce sharp and repeatable cuts severing the cell processes. The cutting appears to work as well with small diameter, unmyelinated axons as with larger diameter, myelinated ones; as well with axons as with dendrites; and as well with processes from cultured embryonic cells as with axons dissociated from adult tissue. Using short edge lengths of 10 microns, the knife was able to cut precisely selected targets within a complex network of dendritic and axonal processes without perturbing surrounding objects (cells and other axons and dendrites) just microns away. Even in the most crowded fields maintained in vitro, with multiple cells in close juxtaposition, it was easy to precisely select individual dendrites or axons and cut only the targeted process.

In further embodiments, undesired lateral motions exhibited by the knife during the cutting stroke that presumably result largely from rotational and lateral compliances in the suspension can be reduced by stiffening a suspension structure as described below along those relevant axes of motion, resulting in sharper cuts. Additionally, it has been deemed desirable to decrease the overall footprint of the suspension structure, currently about 1 mm$^2$, to minimize the possibility of disturbing far-field structures.

Other Uses of the MEMS Nanoknife

The MEMS nanoknife can be used for the cutting of a variety of cells and biological tissues, in research, diagnostics, and health care settings. In addition, they also have utility in the precise sculpturing of fabricated structures for use in tissue engineering and micro and nanofabrication. Furthermore, with appropriate molecular coating of the knife surfaces, the knife can be used as a nano-scaled tool for the precise deposition of chemical and biomolecular reagents at selected targeted regions of interest including on specific cells or tissues. Some examples of these uses of the MEMS knife are provided.

Reproductive Biology

A number of procedures in the area of in vitro fertilization involve tissue cutting. For example, in certain cases of infertility, the creation of an entry point through the outer zona pellucida of oocytes can assist in sperm entry. This assisted entry can result in fertilization in the presence of some motile sperm. Currently, this technique has been carried out using lasers. However, a much less expensive and disposable nanoknife according to specific embodiments of the invention can make such entry points, reducing the costs of such procedures.

In another set of procedures, the zona pellucida region of fertilized eggs undergoes a laser assisted hatching procedure to aid in blastocyst implantation. In assisted hatching, the zona pellucida is thinned using a chemical process or a trench is cut in the zona pellucida using a laser. A nanoknife according to specific embodiments of the invention can be used to weaken the zona pellucida for the same purpose.

Microsurgery—Ophthalmologic Surgeries as Examples.

The small size of the nanoknife makes it highly suitable for use in microsurgical situations. Several examples of its possible use in multiple microsurgical procedures involving the eye are listed below. This list provides a sampling of the range of uses for a nanoknife and is not meant to be exhaustive and suggests additional uses in the areas of but not limited to neurosurgery, reproductive systems, otolaryngology, orthopedics, etc.

Vitrectomy involves microsurgical procedures within the eye for a variety of causes including retinal detachment, complications of diabetic retinopathy, trauma, and various forms of proliferative viteroretinopathies. Available instruments are costly to produce, are not disposable, and are rather bulky for use inside the eye. A nanoknife according to specific embodiments of the invention provides the benefits of a much smaller cutting instrument in the eye, and also limit the size of the openings that to be made in the sclera and thus assist in better wound healing and can provide a low cost alternative that is available for one-time disposable use.

Optic nerve dysfunction can occur due to pressure on the optic nerves and is found in a condition called pseudotumor cerebri. Outside of medical therapy, the current standard of care is the performance of Optic Nerve Fenestration. This procedure involves the surgical exposure of the optic nerve, followed by the used of hand-held surgical scalpels and the manual slicing open of the optic nerve connective tissues to relieve pressure on retinal axons and to save vision. A potential complication with this approach is physician-induced damage to the optic nerve axons. Use of a free electron laser to create openings in the optic nerve connective tissues has the drawback of the general lack of availability of free electron lasers, the expense of this equipment, and the extensive training required to use this technique.

A nanoknife of the invention is small in size compared to existing surgical scalpels and are ideally suited for use in tight spaces throughout the human body where microsurgical procedures must be performed, and not just in the nervous system. Unlike lasers, they can be used with little need to alter standard surgical approaches or exposures. Nanoknives are relatively cheap to produce in a variety of lengths at the micron scale and can be provided as a disposable instrument that is pre-packaged for use in a sterile environment. Nanoknives can be designed with edge-stops so that they can deliver cuts of pre-specified depths, avoiding unintentional damage of underlying tissues.

Tissue Transplantation

Embryological studies often require the transplantation of small pieces of delicate tissues from one part of the developing organism to another. Researchers are often limited by the lack of small-scaled cutting tools, and often resort to homemade instruments that vary a great deal in quality and produce inconsistent results. A nanoknife allows cleaner, more precise harvesting of embryonic tissues compared to current methodologies.

Laproscopic Procedures

The ability of physicians to perform surgical procedures through small incisions with the aid of endoscopic cameras and microsurgical instruments has aided in faster patient recovery. Current surgical instruments for laproscopic use such as scissors, are in the size range of 3-5 mm (length of cutting portion). Microfabricated instruments such as the MEMS nanoknife can easily allow physicians to conduct operative procedures at smaller length scales that is an order of magnitude smaller than is currently possible. This results in more specific targeting of surgical manipulations to a desired tissue location, less trauma, and may lead to new surgical treatments not previously attempted due to lack of proper instrumentation.

Microdissection of Tissue Specimens for Diagnostics

Advances in genomics and proteomics can provide unprecedented specificity in molecular diagnosis. However the optimal use of these resources must be matched by an ability to precisely isolate homogeneous cell populations or subcellular structures to be used for analysis.

Figure 8A:
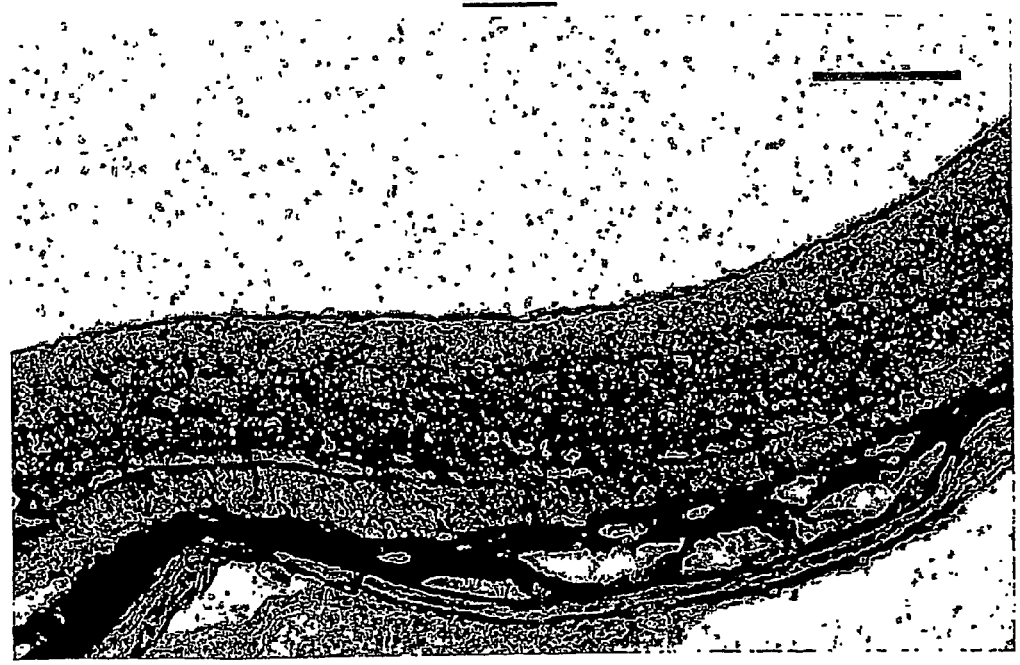
FIG. 8 A-C illustrate three views of a tissue slice of the retina: (A) shows the tissue before section; (B) shows a tissue section after a region is cut out using a nanoknife according to specific embodiments of the invention and (C) shows a cut out region which contains a narrow sliver of retinal tissue (the rest of the material is a plastic supporting membrane).
Figure 8B:
Figure 8C:

A nanoknife according to specific embodiments of the invention can be substituted for a laser such as in laser capture micro-dissection. As an example, FIG. 8 A-C illustrate three views of a tissue slice of the retina: (A) shows the tissue before section; (B) shows a tissue section after a region is cut out using a nanoknife according to specific embodiments of the invention and (C) shows a cut out region which contains a narrow sliver of retinal tissue (the rest of the material is a plastic supporting membrane). In this example, the 8 micron thick tissue slice of the retina is mounted on a polyethylene naphthalene membrane that is itself a few microns thick. The scale bar in the figure is 100 microns. According to specific embodiments of the invention, this type of cutting is done with a knife with a tuned compliance of the knife suspension. A very compliant (or flexible) system as described below is used for cutting soft objects such as axons, while a stiffer compliance is used to cut thicker objects, such as tissue samples.

Isolation of Subcellular Regions for Diagnostics and Research

In addition to harvesting of groups of cells from tissue sections, there is a need in biomedical research for the isolation of subcellular structures to better understand the regulation of biological function within different parts of the cell. Although one method for dissection at a single cell level is currently the use of laser scissors, a nanoknife can be used as a low cost alternative that produces reliable and repeatable cuts.

Cutting of Plant Cells

The introduction of particles and DNA into plant cells is used to study plant cell responses to stress and for plant cell transformation. One important example is the study of plant-microbe interactions. Traditional microinjection methods using glass micropipettes are difficult due to pipette breakage upon penetrating the rigid plant cell wall, and a limitation of the size of the object that can be introduced to the inner diameter of the micropipette. Laser scissors have been used to cut open the cell wall in preparation for bacterial or fungal spore insertion. A nanoknife may be substituted for the laser scissors and used to make cuts in plant cells to allow microbes and DNA to gain entry into the cell interior.

Cutting of Microfabricated Structures

In addition to cells and tissues, nanoknives may be used for the cutting and shaping of organic structures that are produced for uses in tissue engineering. This includes scaffold structures within which cells are seeded for subsequent growth. The MEMS Nanoknife can aid in the precise sculpting of these tissue-engineered structures to achieve implantable structures of a specific size, and shape, and 3D features to be used in targeted locations in the body.

A similar use of a nanoknife can be applied for the sculpting of MEMS devices created out of PDMS molding. Such sculpting can potentially create useful features in microdevices that either cannot be or are difficult to synthesize using traditional modeling and stacking procedures.

Cutting of Macromolecular Assemblies, Chromatin

Given the radius of curvature of the knife edge in the nanometer scale range, the nanoknife can also be used to cut subcellular biological assemblies including microtubules (100 nm diameter), mitochondria (100 nm to 1 microns), and chromatin.

5. Self-Leveling Knife

Figure 9A:
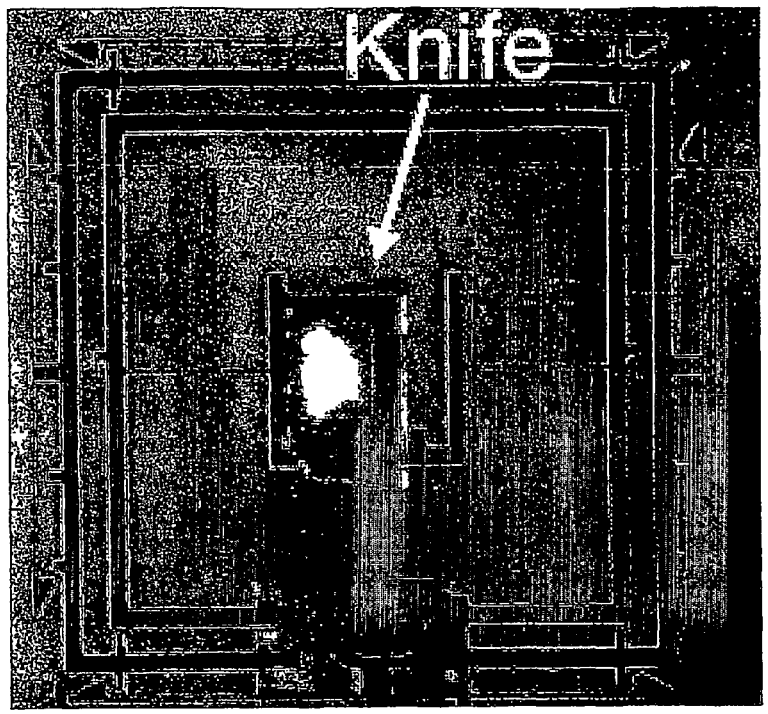
FIG. 9A-B illustrate an example novel nanoknife design with compliant leveling frame in a modular design according to specific embodiments of the invention, with example dimensions of one mm×one mm×100 microns thick.
Figure 9B:
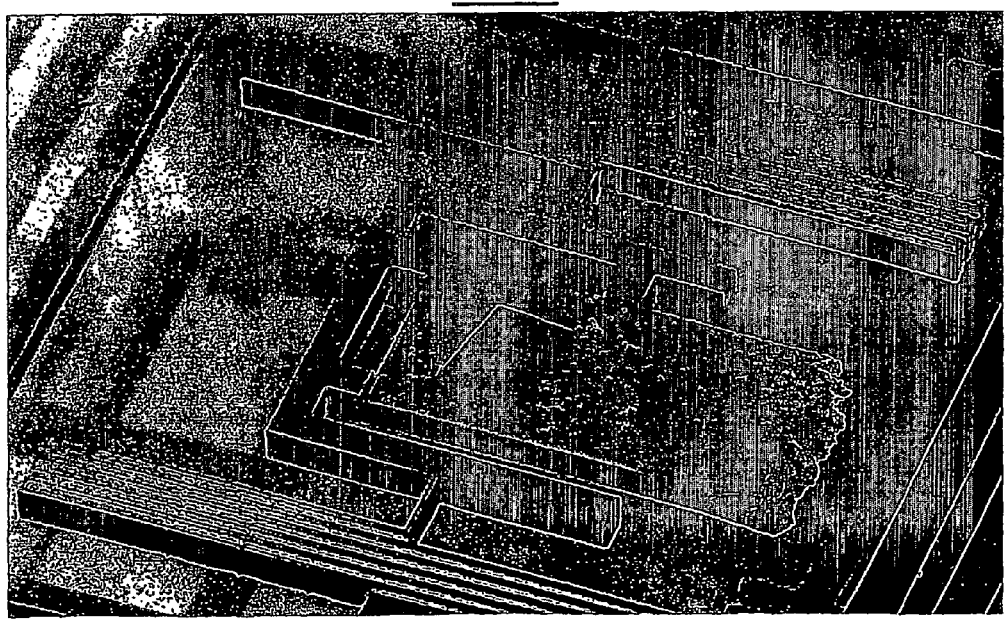

In further embodiments, the invention provides a nanoknife with a self-leveling mechanism that automatically aligns the knife edge with a cutting surface. Such a self-leveling frame was used in a number of the example use demonstrations discussed above. Example nanoknives fabricated and assembled within compliant frames are shown in FIGS. 9A and B. While a variety of dimensions can be selected for such a knife frame, depending on application, one example dimension for the illustrated frame is approximately 1 mm$^2$ by approximately 100 microns thick. In FIG. 9A, a nanoknife can be seen suspended between two planar "springs" fabricated in a silicon substrate. The pliant nature of the silicon provides enough flexibility to assist the microknife is self-leveling during manipulation of materials at the tip. Also seen in the figure are portions of interlocking structures at each outer corner that can be used as described below optionally to assemble the self-leveling knife into a 3D frame. FIG. 9B shows a close-up example of a similarly-mounted nanoknife.

6. Example MEMS Axon Surgery Platform

According to specific embodiments of the invention, the invention is involved with a multifunctional 3D MEMS surgical platform. The individual MEMS component modules are designed to be interlocking and assemble together to form the complete MEMS surgical platform, with MEMS modules are configured within a space frame. In specific embodiments, a carrier device couples the platform to external control. While the invention is here described with reference to axon surgery, there are many other applications of the MEMS construction methods and/or modules described herein.

Precise cutting is facilitated by using a self-actuation method in some embodiments, rather than operator initiated knife movement by a micromanipulator. Self-leveling and actuation are incorporated into a specific example design for a MEMS axon knife module according to specific embodiments of the invention as described in detail below. This module uses thermal actuation and a compliant self-leveling frame for knife alignment.

Assembly of Multifunctional MEMS Platform

According to specific embodiments of the invention, a MEMs platform can be understood and/or constructed as a number of modules in a space frame. FIG. 10A-G are a series of block diagrams' illustrating the architecture and a method for assembling a space frame with optional assembled MEMS modules according to specific embodiments of the invention. An example assembled platform (modules & space frame) is approximately 1 cubic millimeter in size.

Figure 10A:
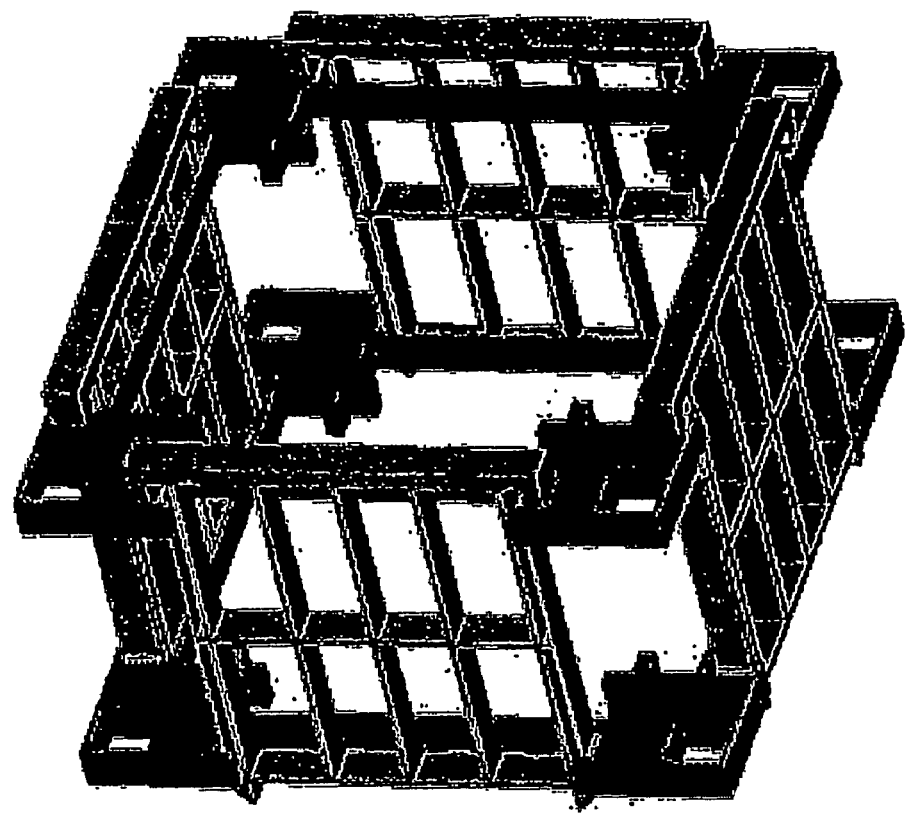
FIG. 10A-G are a series of block diagrams illustrating the architecture and a method for assembling a space frame with optional assembled MEMS modules according to specific embodiments of the invention.

FIG. 10A illustrates a space frame alone according to specific embodiments of the invention. As can be seen, this space frame can be constructed from six planar pieces into a box-like form. While the illustrated space frame is roughly a cube, other configurations are possible. In one assembly method, the six planar pieces of the space frame are constructed of interlocking pieces and assembled as further described herein. However, other fabrications methods can be used to create a space frame, such as direct 3D fabrication. According to specific embodiments of the invention, carrier holes are provided at the eight corners of the space frame, to allow for the use of a carrier platform to carry and position the space frame and the MEMS modules as further described herein. As an example, the dimensions of such a frame are 1 mm×1 mm×1 mm.

Figure 10E:
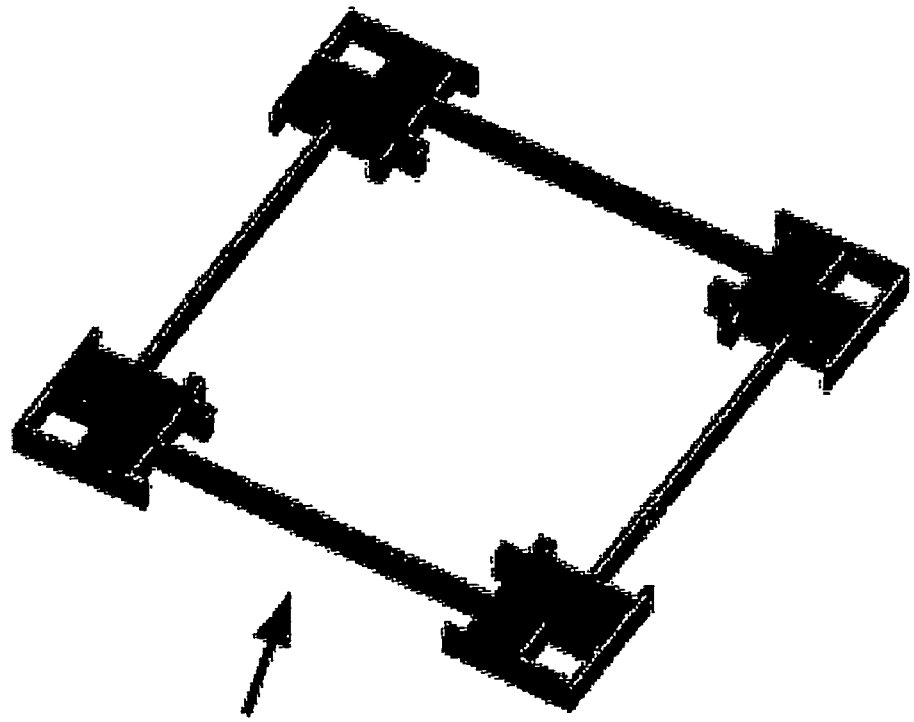
Figure 10B:
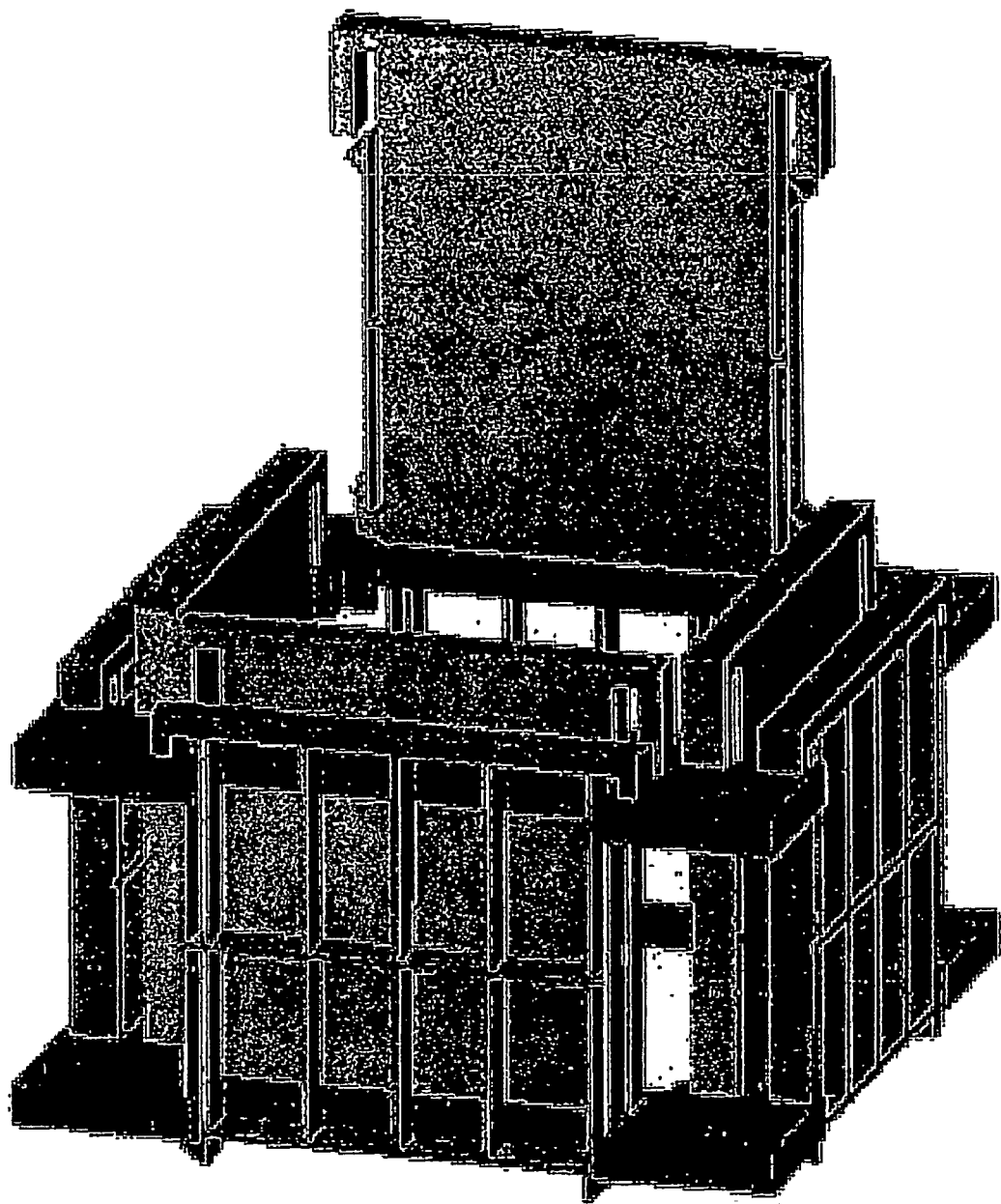

FIG. 10B illustrates insertion of MEMS modules (shown in FIG. 10B as generic, light blue structures) into the space frame. These modules can be any devices of the appropriate dimensions that optionally are provided with an interlock as described herein. In many applications, it is anticipated that this modules will be MEMS devices, but they can also be various hybrid devices, including devices that include but are not limited to electronic circuit components, nucleotide array components, chemical, and biological components, etc.

Figure 10C:
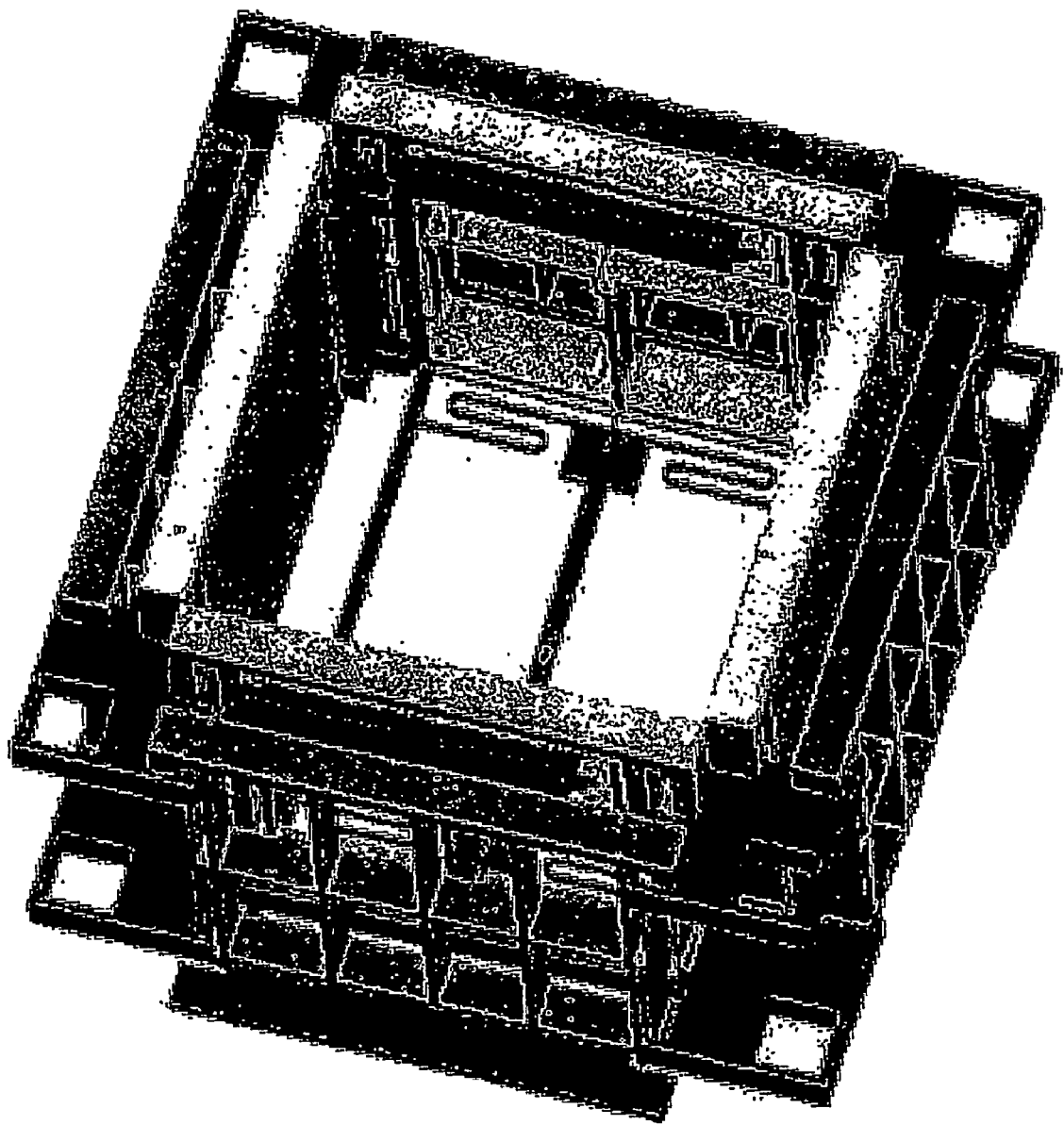
Figure 10D:
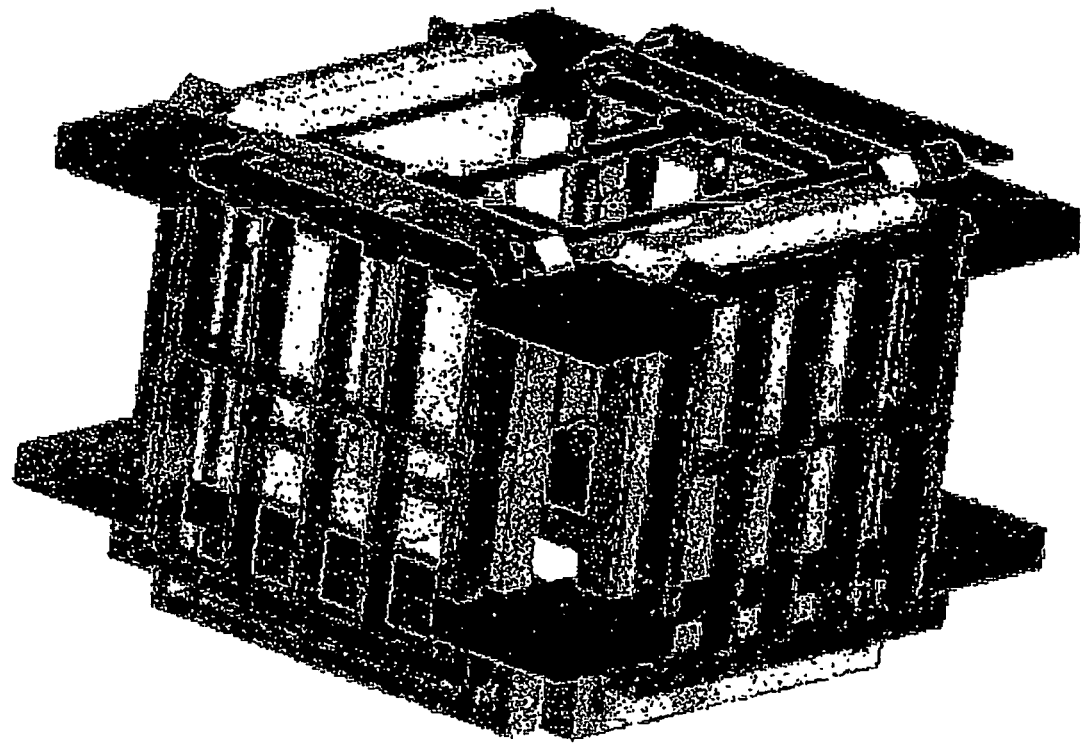
Figure 10F:
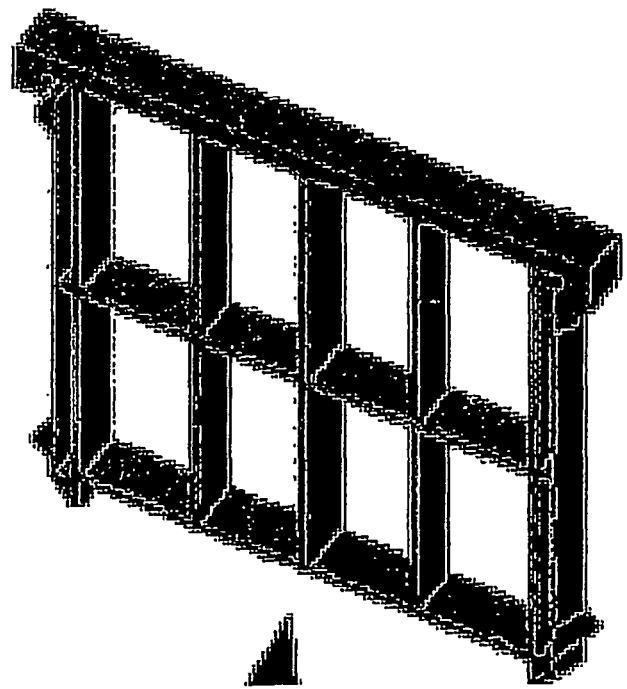
Figure 10G:
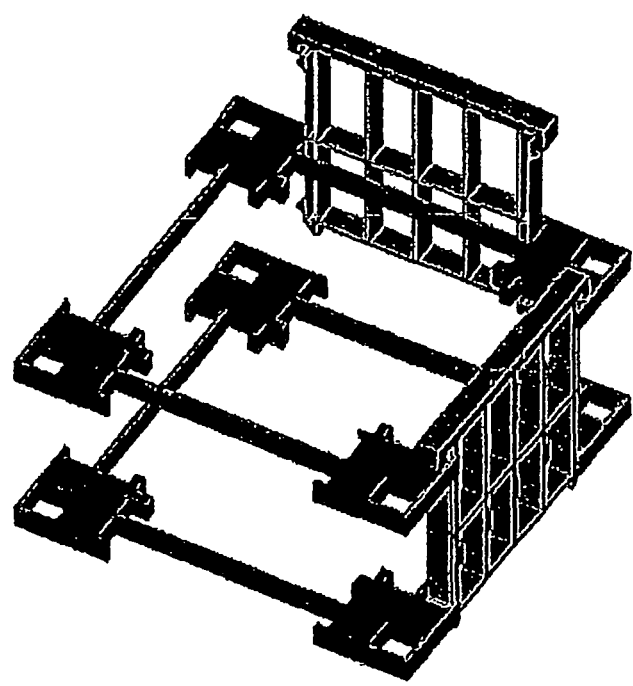

FIG. 10C illustrates an oblique view from top showing space frame with an MEMS knife module inserted in two side slots of the space frame and generic modules in the other two slots. The electrode module and other components that may also be inserted in the other two slots are omitted for clarity. FIG. 10D illustrates an oblique view from the bottom showing space frame with a knife module inserted. FIG. 10E and FIG. 10F illustrate separate sides of a space frame according to specific embodiments of the invention, each having example dimensions 1 mm×1 nm×100 microns thick. FIG. 10G illustrates and example of assembling a space frame.

According to specific embodiments of the invention, interlocking latching features are designed into each of the modules for self-fixation and to facilitate assembly. Assembly can be performed, for example under a stereomicroscope using micro-grippers and other probes. Individual modules can be switched in and out as needed for experimentation and with improvements in module design.

Example Constructed Nanoknife System

Figure 11A:
FIG. 11A-D are scanning electron micrographs illustrated an example assembled MEMS nanoknife device and showing: (A) modular components against a penny for size comparison; and (B-D) three views of a 3D self-leveling frame holding a nanoknife according to specific embodiments of the invention.
Figure 11B:
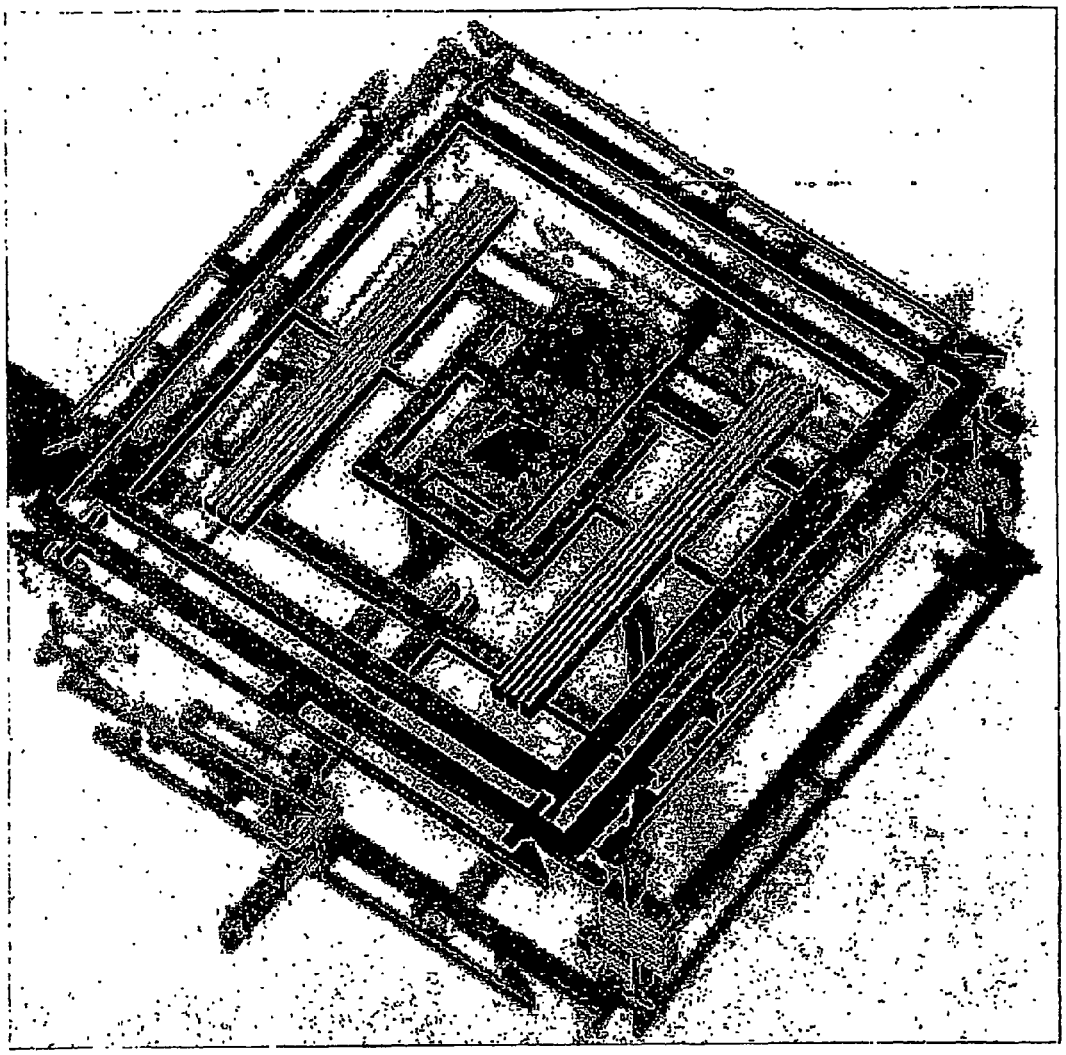
Figure 11C:
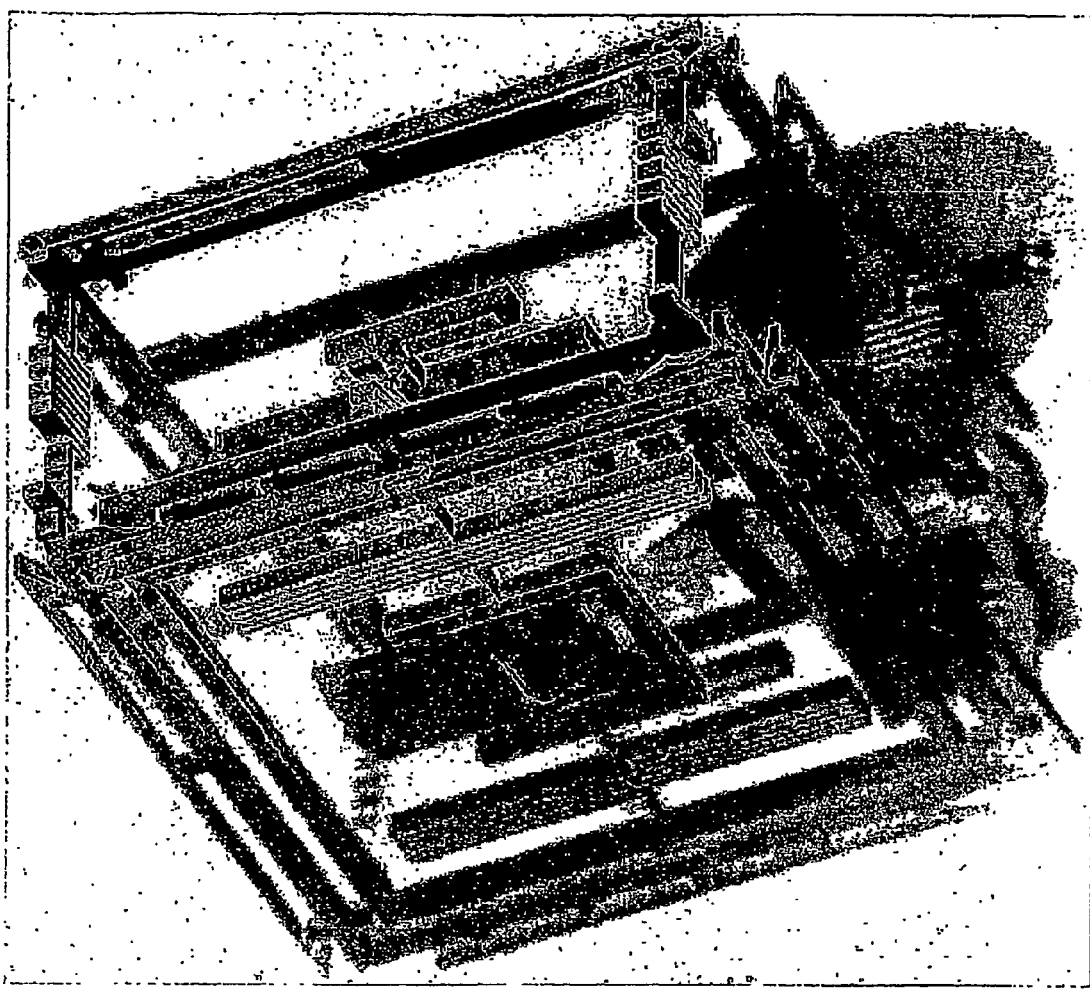
Figure 11D:
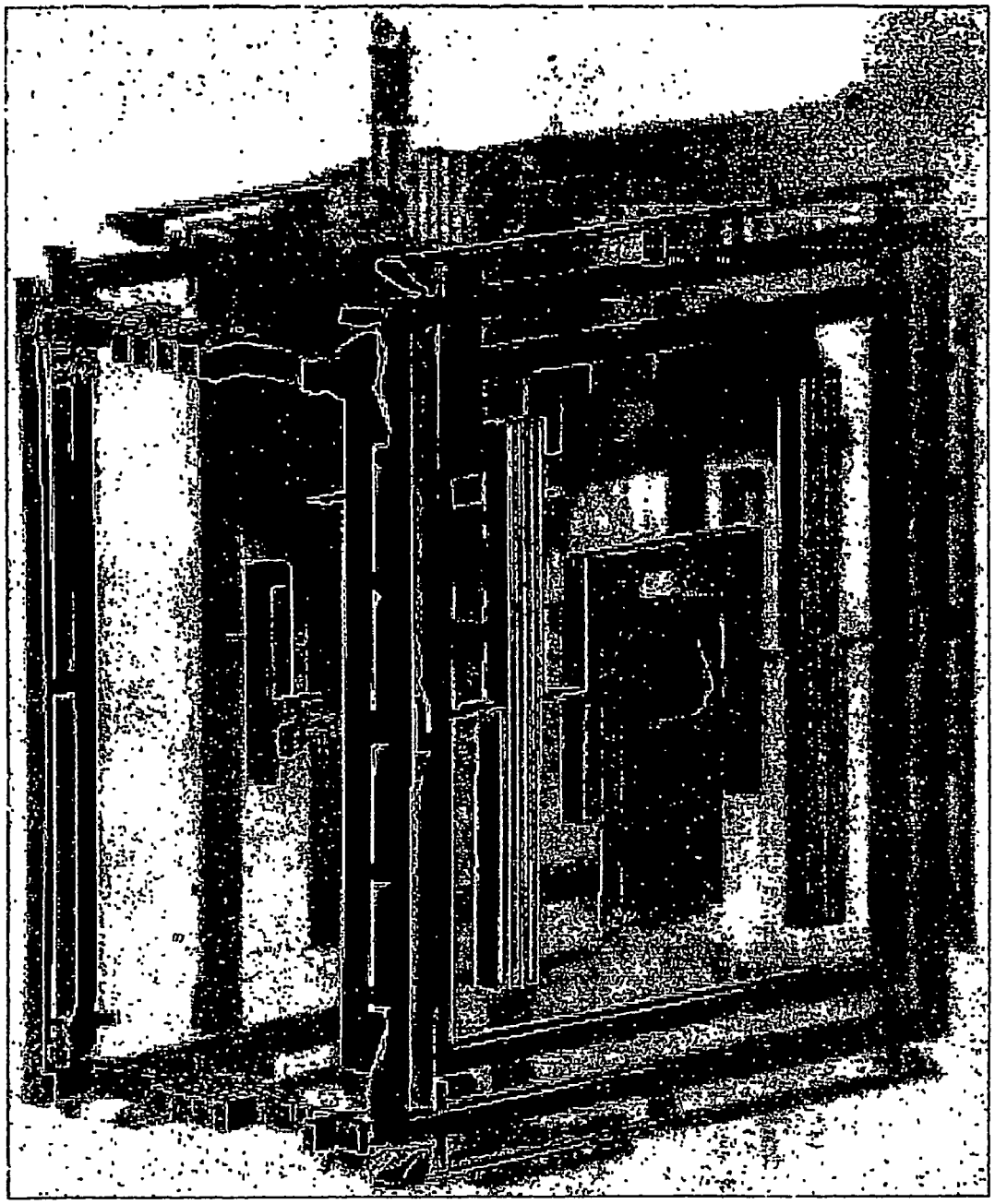

FIG. 11A-D are scanning electron micrographs illustrated an example assembled MEMS nanoknife device and showing: (A) modular components against a penny for size comparison; and (B-D) three views of a 3D self-leveling frame holding a nanoknife according to specific embodiments of the invention. In these figures can be seen examples of an interlocking feature that can be used to hold together microfabricated structures. The design of the locking mechanism is such that the tension provided by the deformation of, for example, microfabricated silicon structures will keep the pieces in place. FIG. 11A shows an example wherein a 3D self-leveling prototype platform is assembled from approximately 16 individual pieces; for example a knife frame with two in-plane "spring" structures; eight separable "spring" structures, and other supporting frames. A prototype device was assembled using both interlocking mechanisms and adhesive.

Fabrication

The example microdevices as shown in FIG. 10 and FIG. 11 are each formed from a number of modular pieces that can be fabricated using standard silicon fabrication techniques or other techniques able to fabricate structures at the desired scale. Many such techniques are well-understood in the solid state art and adaptation of these fabrication techniques to make the components of the present invention will be well understood to those of skill in the art.

Assembly

Various strategies have been developed for assembling MEMS device, including automated manufacturing and assembly. Any MEMS assembly techniques can be used for assembling a surgery platform device according to specific embodiments of the invention. Assembly of a space frame and MEMS surgery platform according to specific embodiments of the invention can also use microtweezers and grippers designed for use with microfabricated structures. A variety of microtools with different tip sizes and shapes for specific uses are available, and examples of such tools are shown in FIG. 12. These microtools utilize a thermal actuation mechanism and are capable of delivering up to millinewtons of force. A microtweezer holding a MEMS axon knife is shown in FIG. 12B. Such microtools have been used to assemble a MEMS retinal implant in which spring-loaded electrodes are used for retinal axon stimulation within the eye (Okandan et al., 2003).

Example Carrier

In particular applications, a MEMS device, such as shown in FIG. 10 is used with a specifically designed carrier to be precisely placed where desired and to interface with other equipment, such as by electrical contacts.

Figure 13C:
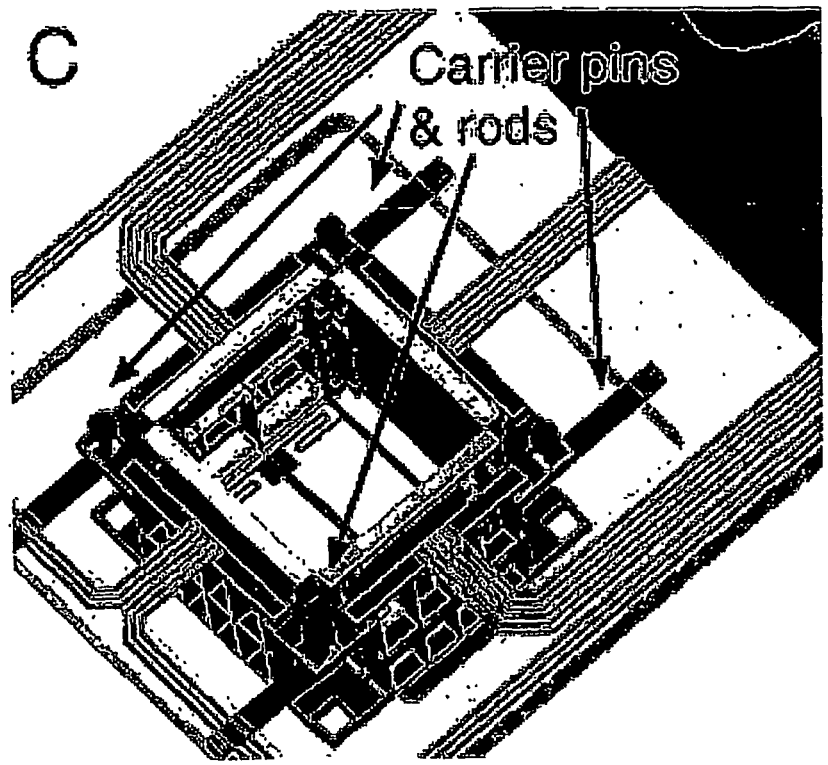

For example, after assembly, a MEMS surgical platform (assembled MEMS modules and space frame) can be precisely positioned over the axons selected for experimentation using a platform carrier, as illustrated in FIG. 13. This platform carrier provides a method of uncoupling the platform mechanically from the external world, while mechanically stabilizing it for example with respect to the axons to be cut. In addition, the carrier can provide an electrical interface to supply power to the surgical platform e.g., for actuation, DEP, electrofusion and for other uses. In turn, the carrier can be connected to a micromanipulator (e.g., a Sutter MP285) through a handle at one end, indicated by the green arm in the figure.

According to specific embodiments of the invention, the space frame is supported within the carrier via a set of angled rods (depicted as blue structures in the figure) that insert into the corners of the space frame, with a cap attached (e.g., by glue) onto the rod to prevent slippage from the space frame with the other end of the rod attached to the carrier. An alternative to the coupling pins and rods is to use low stiffness silicon to tether the space frame to the carrier device. Such a tethering mechanism has been used in the MEMS components of dynamic air bearing magnetic recording heads in disk drives. Once in place, the space frame together with the MEMS platform can be positioned using the micromanipulator. At a desired position over the selected axons, the micromanipulator will be lowered and the bottom of the space frame will contact the surface of the glass. The micromanipulator is then lowered an additional amount, allowing the carrier to drop away free of the space frame, thus removing mechanical coupling between the MEMS platform and the carrier as well as the micromanipulator. A similar mechanism for mechanical uncoupling is used in scanning tunneling microscopes.

Electrical Connections

A variety of different electrical connectors can be used in a MEMS platform according to specific embodiments of the invention. For example, MEMS Precision Instruments (MEMSPI, at www.memspi.com) has developed proprietary MEMS electrical connectors that are made separately and then clipped on to the silicon structure to either form ohmic contact with the silicon or remain isolated by oxide. The connector components are Bosch etched silicon structures coated with sputtered aluminum or gold depending on the application. User replaceable modules make and break sliding contact by virtue of compliant cantilevered gold-coated silicon beams. For use in an aqueous environment, the sliding contacts are located within a trapped air pocket with hydrophobic surfaces. Wires (Al or Au, 25 micron diameter) are inserted into barbed grips patterned at the edge of the connector using microfabricated tools.

Example MEMS Axon Knife Module

Figure 14A:
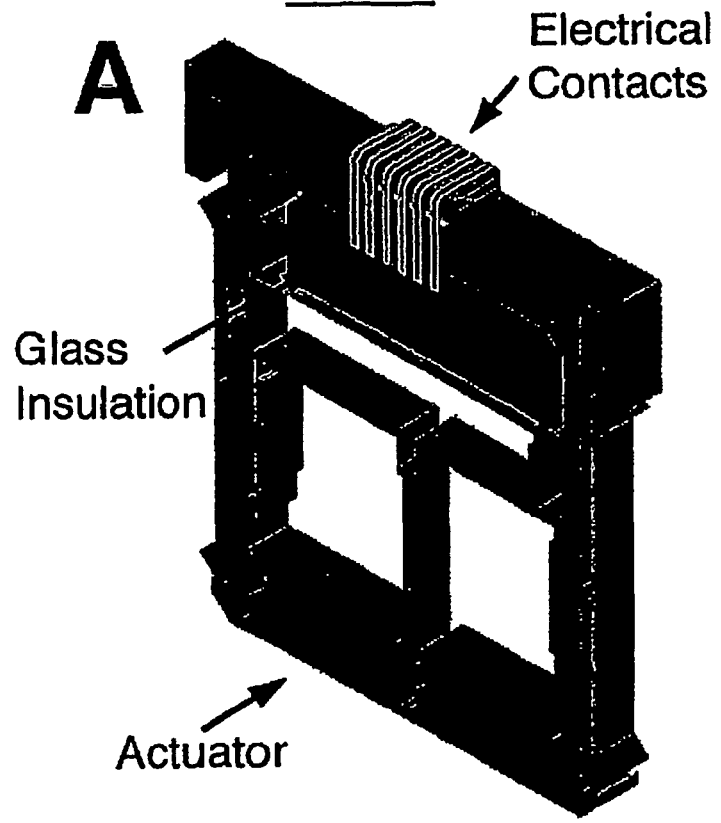
FIG. 14A-C are diagrams illustrating an example nanoknife module according to specific embodiments of the invention showing (A) a thermal actuator with gold plated electrical contacts (illustrated in yellow) and glass insulation around the heated beam (shown in blue); (B) two thermal actuators with a flexible frame (brown) containing a nanoknife; C) higher magnification of the underside of the module with knife (purple structure).
Figure 14B:
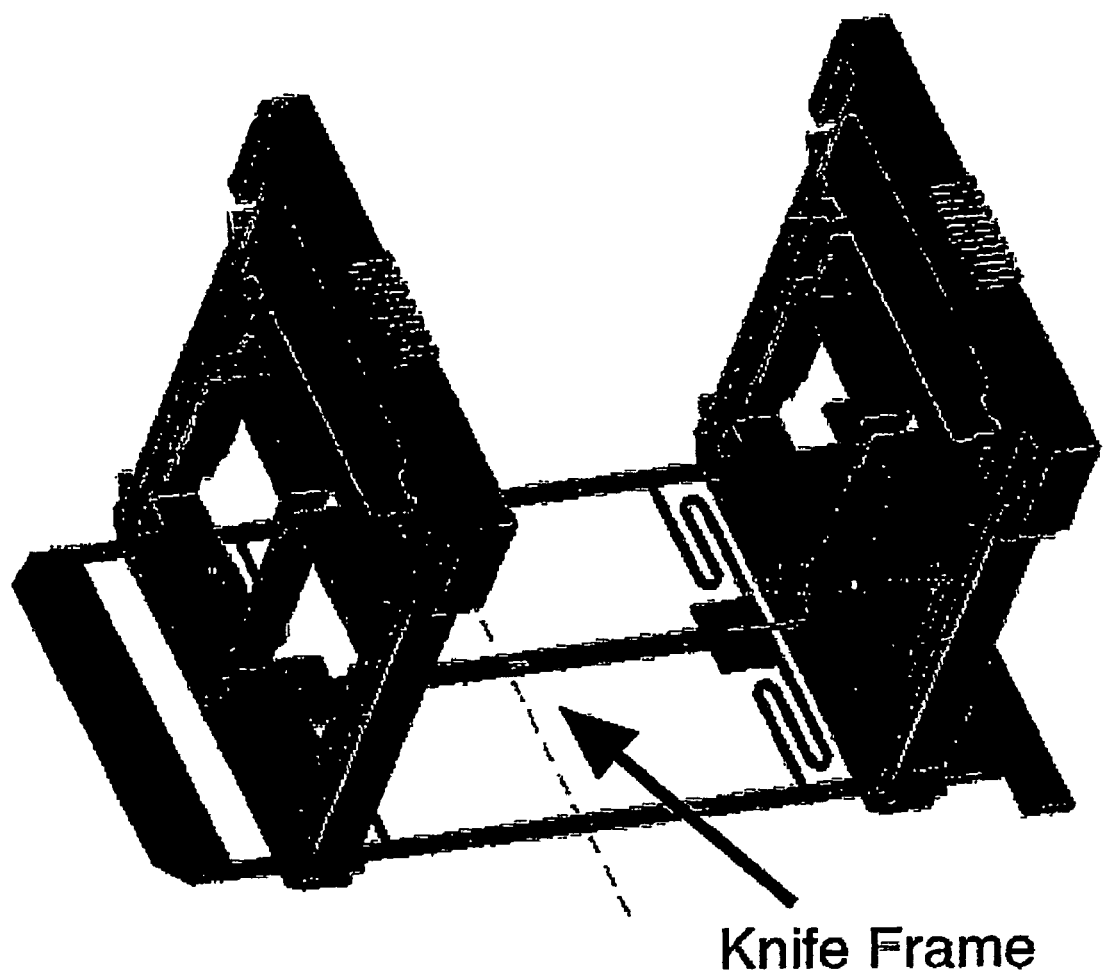
Figure 14C:
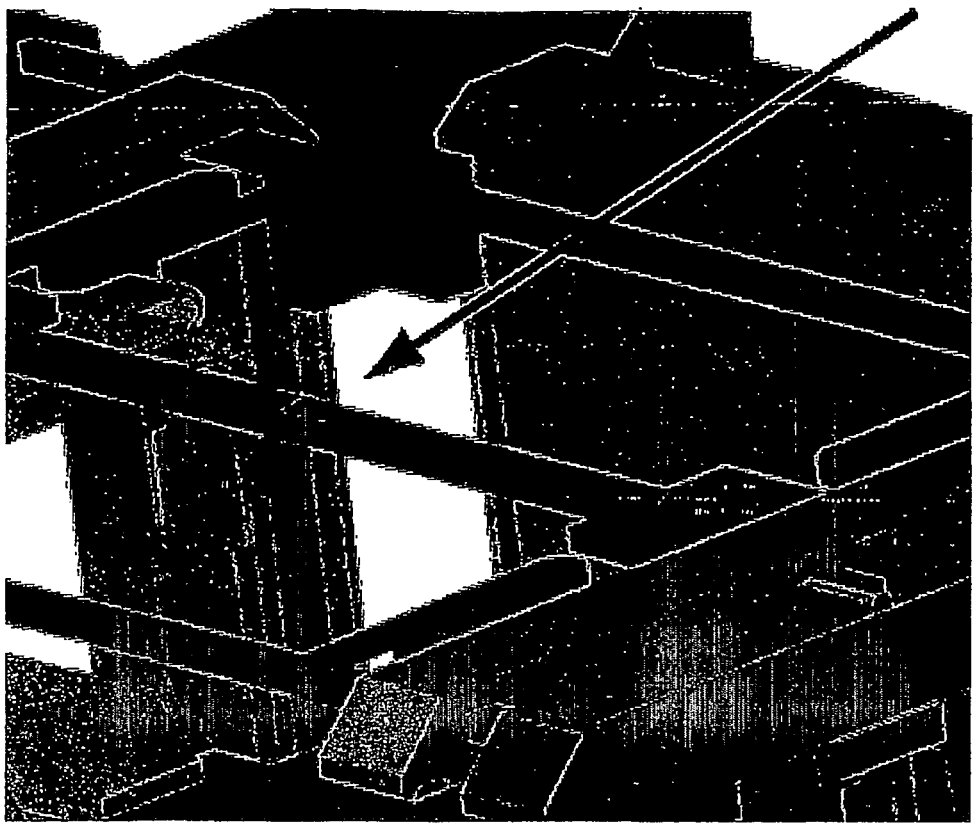

An example module that can be used in a MEMS platform frame according to specific embodiments of the invention is a MEMS axon knife, as shown in FIG. 14. This example MEMS axon knife module consists of two thermal actuators (FIG. 14A) that are interconnected at their bottom ends by a flexible knife frame (FIG. 14B). In this example, thermal actuation is used to drive the up and down motion of the center beam of the flexible frame to which the knife is attached (FIG. 14C).

Figure 15:
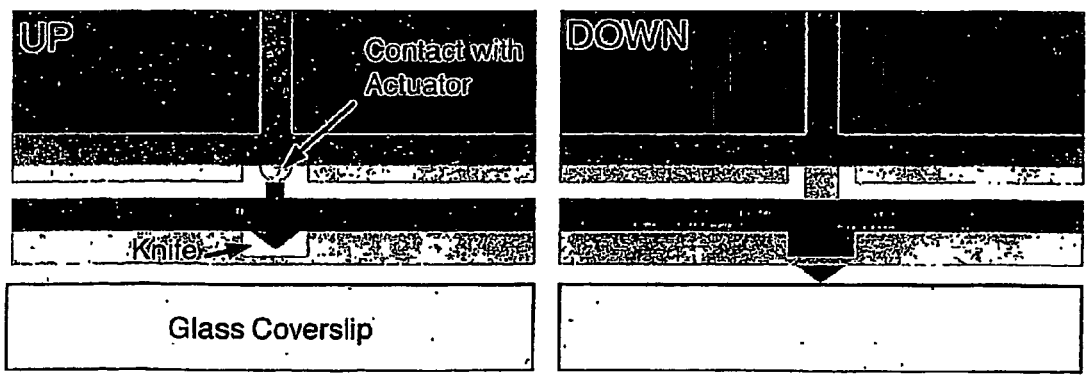
FIG. 15 is a block diagram illustrating end-on views of the center bottom portion of an example knife module according to specific embodiments of the invention and indicating "up and down" movement of the knife with respect to a cutting surface.

In this example, in the "UP" position (FIG. 15), a spacing of 10 microns exists between the knife-edge and a cutting surface, for example a glass coverslip forming the bottom of a tissue culture dish for in vitro cutting. Given that for example retinal axons are 1-2 microns in diameter, there is sufficient spacing to position the knife module over any desired position in the culture dish. In the "DOWN" position, thermal expansion of the actuation mechanism leads to downward movement that impinges on the two ends of the center beam of the knife frame. The downward movement of the frame brings the cutting edge of the knife down to a cutting surface. In an example implementation, the speed of the downward stroke is 20 microns/sec. The retraction of the knife back to the "UP" position is initiated by interruption of the applied voltage and occurs at 20 microns/sec. The force is determined by the stiffness of the beams and can be designed to range for example from 1 micronewton to 1 millinewton.

Using this type of MEMS axon knife module, the excursion limit of the knife can be controlled and a cutting stroke consisting of one cycle of down and up movement of the knife can be automated. After the mechanical uncoupling of the space frame containing the knife module from the carrier platform, the knife module will rest on the glass surface on its own at four points. As a result, the long axis of the knife-edge is automatically aligned with the plane formed by the bottom of the culture dish. This self-leveling mechanism enables precise axon cutting without distortion.

Glass Insulation for Thermal Actuation

According to specific embodiments of the invention, a thermal actuation module can use an insulation region (such as glass) to improve actuated performance. An example of such a region includes proprietary insulation techniques for the operation of thermal actuators in fluids developed by MEMSPI. The heated silicon beams of the thermal actuator are enclosed within a Pyrex™ capillary or between thin Pyrex sheets to control the rate of heat loss to the environment. The mechanical connections at the ends of the actuator beams to the device are also Pyrex with reflowed glass frit to limit heat flow into the supporting silicon mechanism. To deliver power to the thermal actuator, insulated gold or aluminum wires (25 micron diameter) are inserted into barbed ohmic contacts using micro tools. The open end of the enclosure is hydrophobic to exclude water. The trapped air within the enclosure expands and contracts as the actuator heats and cools. As the air expands it starts to form a bubble extending out into the water, but not enough to break free.

Example Actuation Methods

A MEMS axon knife must be able to deliver an actuation force for cutting. A number of actuation principles have been used to control mechanical movements in MEMS devices. Some of the more common include electrostatic, piezoelectric, magnetic, and thermal expansion (Madou, 2002). Other forms of actuation include bubble generation by heat or electrolysis to deliver force, and the use of titanium nickel shape memory alloys to deliver motion on command. Magnetic actuators are difficult to control given that force generation is non-linear with respect to applied input. Complex design features are necessary for useful actuation. Piezoelectric actuators have a fast response time and if designed with sufficient leverage, these actuators can generate high forces. Their main disadvantage is the requirement for high operational voltages that are typically over 100 volts. Electrostatic actuators are fragile and prone to fail especially in situations where biological tissue debris may compromise the actuation mechanism. In addition, high voltages in the range of 100 V are also required and force generation is relatively weak in the range of nanonewtons. Gearing mechanisms are required for the production useful forces. In terms of actuation within a BioMEMS device to be used on tissues, thermal expansion provides a reliable means of force generation. Silicon based thermal expansion actuators are robust, simple to fabricate, and relatively resistant to mechanical seizing. The required operational voltages are low and when combined with suitably designed levers to improve displacement, the amount of force generated can be in the millinewton range (Keller and Howe, 1995, 1997). The use of thermal expansion actuators in an aqueous environment can be achieved by insulation with a suitable material to isolate the hot and cold regions of the actuator. Recent work for example have reported the use of paraylene C polymer layers to insulate a platinum metal thermal actuator designed to operate in aqueous environments (Chan and Li, 2002). Another insulating material for use in conjunction with thermal actuation in an aqueous environment is glass. MEMSPI has developed methods for glass insulation of heated silicon beams within thermal actuators (described below). Thus, while any of the above mentioned actuation methods can be used with a nanoknife according to specific embodiments of the invention, a presently preferred method is thermal expansion as described in more detail below.

Example MEMS Electrode Module

A further example module that can be used in a MEMS platform frame according to specific embodiments of the invention is a electrode module, as shown in FIG. 16. This example module includes two electrode arrays, each connected to a module for inserting into the frame. When inserted into an example flame, the electrodes are placed next to an example nanoknife, as illustrated in FIG. 16A. In specific embodiments, these electrodes are patterned with pin contacts as shown in FIG. 16B. Both electrode configurations will be patterned onto the ends of beams (yellow structures in FIG. 16A) within the electrode module. The two electrode arrays, each connected to a beam, are positioned along either side of the MEMS axon knife. During use, the electrode arrays will be located above the axons and the cutting surface. The distance between the axons and the electrode arrays in an example system are fixed at about 30 microns.

7. Example Uses of Microsurgery Platform

Cutting Host and Donor Axons

In one example use, a MEMS axon knife can be used to cut both the host and donor axons in preparation for a donor axon nerve repair process. In order to achieve proper alignment, axons are trimmed so that sufficient length remains for the ends of the two axon segments to meet. An ideal axon cutting protocol should therefore not only provide efficient cutting, but also reliably leave both axon segments ends with adequate length and their ends at appropriate positions for subsequent alignment. Thus, according to specific embodiments of the invention, a MEMS axon knife is used to simultaneously cut both the host and donor axons at roughly 60 degrees to the long axis of the axons to generate four axon segments (as illustrated labeled a-d in FIG. 17). In the figure, segment a can be understood as connected to the host neuron, segment d is part of the donor axon, while b, c are the two extraneous segments resulting from the cut. Segments a, d will be selected for fusion with each other, while segments b, c will be moved aside and prevented from interfering with the fusion process.

Advantages of an Assembled MEMS Axon Surgery Platform

Using modular MEMS devices that are assembled within a space frame provides several advantages according to specific embodiments of the invention. Firstly, the ability to switch in or out individual modules without affecting the other components of the platform facilitates testing and design optimization. Secondly, modules can be designed so that following assembly within the space frame, the functional elements of the modules are already pre-arranged optimally to carry out specific tasks. For example, the placement of electrodes immediately adjacent to the axon knife allow for the quick transition from cutting to DEP and fusion. This pre-positioning minimizes the need for movement within MEMS devices and facilitates automation of axon repair. Thirdly, the arrangement of MEMS modules in an open space frame permits convenient optical visualization during experimentation. This greatly aids in the selection of axons to be studied and the analysis of axon behavior at different stages of the repair process. Lastly, additional features can be readily incorporated into the platform. One area of potential interest is the use of microfluidics to control the local fluid environment around the axons. This control may be useful for the quick exchange of fluids of different conductivities as part of DEP. In addition, microfluidics may also be helpful in the delivery of proteins, pharmacological agents, or macromolecules to assist in axon repair.

The assembly of multiple MEMS components into a 3D platform creates multifunctional devices that are well suited for in vivo microscale cell surgery and tissue sampling. In conventional BioMEMS diagnostic devices, cells or cellular components such as proteins and genetic material already isolated from patients are brought into the device and passed serially along analytical stations. BioMEMS devices designed for use on a specific cell in vitro or in vivo must bring multiple functions to bear onto a given cell that remains fixed in place. The assembly of multiple MEMS components into a 3D superstructure greatly expands the range of functional capabilities that are possible in a single device beyond the limit imposed by traditional wafer processing techniques.

8. Manipulation and/or Fusion Using Electrical Signals

According to specific embodiments of the invention, the invention provides methods and/or systems to facilitate the movement of very small structures (such as axons) and particular behaviors of these structures (such as fusion) using electric fields. In further embodiments, these methods and/or systems are combined with an example nanoknife as described herein into a small scale platform (e.g., approximately 1 cubic millimeter, or 0.1 cubic millimeter to 10 cubic millimeters) for performing very small scale manipulations.

Thus, in a specific example platform used for discussion purposes, following cutting, host and donor axon segments are aligned for subsequent fusion. According to specific embodiments of the invention, dielectrophoresis (DEP) is used as a preferred manipulation method for use with the MEMS axon surgery platform. DEP is the movement of polarizable objects in a non-homogeneous electrical field and was first described by Pohl in 1978. In essence, objects in an alternating electrical field will experience field-induced polarizations on their surfaces. In the presence of a homogeneous field, dipole forces will alternate on an object's surface along with alternations in the electrical field, but no net movement of the object will occur. However, in a non-homogeneous field with gradients of field strengths, the object will experience a net force in one direction, causing it to move towards one side of the electrical field. DEP is distinct from electrophoresis in which the net charges on an object lead to its movement in one direction within a stationary electrical field.

The theoretical basis for DEP in specific instances can be further described as follows: The dielectric force $F_{DEP}$ acting on an object with radius=r, in an electric field E, is described as:

$$F_{DEP} = 2\pi r^3 \varepsilon_m \text{Re}[\overline{f}_{CM}]\nabla |E|^2 \qquad (1)$$

where $$\overline{f}_{CM} = \text{Clausius-Mossoti factor} = \frac{\varepsilon_o - \varepsilon_m}{\varepsilon_o + 2\varepsilon_m}$$

$\varepsilon_o$ = permittivity of suspended object, $\varepsilon_m$ = permittivity of the medium $$\varepsilon = \varepsilon - j(\sigma/\omega),$$

where $$j = (-1)^{1/2}$$

$\sigma$ = conductivity $\omega$ = angular frequency of applied voltage (The imaginary part of the equation related to out of phase components has been omitted. For details see Gascoyne and Vykoukal, 2002)

The formula above shows that DEP force is related to the magnitude and AC frequency of the applied voltage, the size of the object, and the dielectric properties (permittivity and conductivity) of the object and of its surrounding medium. In practice, the magnitude of the voltages that can be applied to objects in a fluid environment is limited as high voltages lead to electrolysis of water when the electric field frequency is low. As a result, DEP forces are most useful for manipulation of small objects such as bacteria (0.5-2 microns) and cells (5-30 microns) at field frequencies above at least 5 kHz.

Dielectric Properties of Cells

The frequency-dependent complex dielectric properties of objects can arise from electronic, permanent dipolar, electrical conductivity, or interfacial (Maxwell-Wagner) mechanisms of polarization (von Hippel, 1995). Because different cell types are morphologically distinct, they have different intrinsic dielectric phenotypes (Gascoyne et al., 1997a). Using this approach, it has been possible to separate breast cancer and leukemia cells from other cells in blood, malaria infected cells from uninfected cells, and live cells from cells undergoing apoptosis (Gascoyne et al., 1997b; Wang et al., 2002).

Parameters for Controlling DEP

The formula above indicates that a number of parameters can be used to control DEP. For example, the DEP forces on objects in a medium are governed by a relationship between the dielectric properties ($\epsilon$) of the object and the surrounding medium defined by the Clausius-Mossoti factor, which indicates that DEP forces are generated when the dielectric properties of the object and its medium are significantly different from each other. In fact, the sign of the difference in the polarizability of the object compared with its surrounding medium will determine the direction of its movement in opposite directions within an alternating electrical field. An object that is less polarizable than the medium will be directed away from the strongest part of the field and is said to exhibit negative dielectrophoresis. An object that is more polarizable than the medium will move towards the strongest part of the field and is said to exhibit positive dielectrophoresis. Although dielectric properties of objects are intrinsically determined, the medium conductivity can be altered to influence the magnitude and direction of DEP force generated. In practice, positive DEP is achieved by lowering the conductivity of the surrounding medium in comparison to the internal conductivity of the cell. Although negative DEP may be theoretically achieved by increasing the conductivity of the surrounding medium, generally the medium will heat up and this might impact cell viability. Thus, it is presently believed that positive DEP is more effective in manipulations of cells and/or cell portions as discussed herein.

The frequency of the applied voltage can also be used to precisely control the magnitude and direction of DEP and it has been found that at certain so-called crossover frequencies, the DEP force traverses zero as its direction reverses. At applied frequencies below the crossover frequency, cells experience repulsive DEP forces. At higher frequencies, the cells experience attractive DEP forces. For a given frequency, the magnitude of the DEP force acting on the different cell types can vary substantially. This frequency dependent behavior represents a convenient way of delivering different DEP forces to specific cell populations within microdevices through appropriate selection of the DEP field frequency. (Further information in Yang et al., 1999).

DEP Manipulation of Elongated Cellular Structures

DEP crossover frequencies are determined not only by cellular composition, but also by cell shape and diameter. While spherical cells exhibit isotropic responses to an applied field, DEP forces may be anisotropic for non-spherical cells. For example, in a medium of 56 mS/m conductivity and at frequencies of 50-100 kHz, erythrocytes become oriented so that the flat dimension of their biconcave disk shape lies parallel to field lines (Miller and Jones, 1993). This arises because the crossover frequency perpendicular to the thin plane of the discoid body is higher than the crossover frequency along the long axis. This orientation effect becomes more marked as the cell shape becomes more and more elongated. For example, the tail of a sperm exhibits a crossover frequency along the length of the tail that is almost two orders of magnitude lower than that perpendicular to the tail. The behavior of elongated structures in DEP fields is of particular interest with respect to the use of DEP to manipulate axons. According to specific embodiments of the invention, the application of a correct frequency matched with an appropriate electrode design allows the controlled movement of axon segments.

Cell Viability after DEP

Investigations have indicated that axon physiology is not substantially affected by DEP. Effects on cell proliferation can be eliminated or substantially reduced by the addition of catalase to convert hydrogen peroxide to water and oxygen in some situations (Wang et al., 1999). DEP parameters typically used for cell manipulation (10 kHz to 1 MHz, conductivities of 50 mS/m or less) have been shown not to affect cell membrane integrity and viability.

Figure 18:
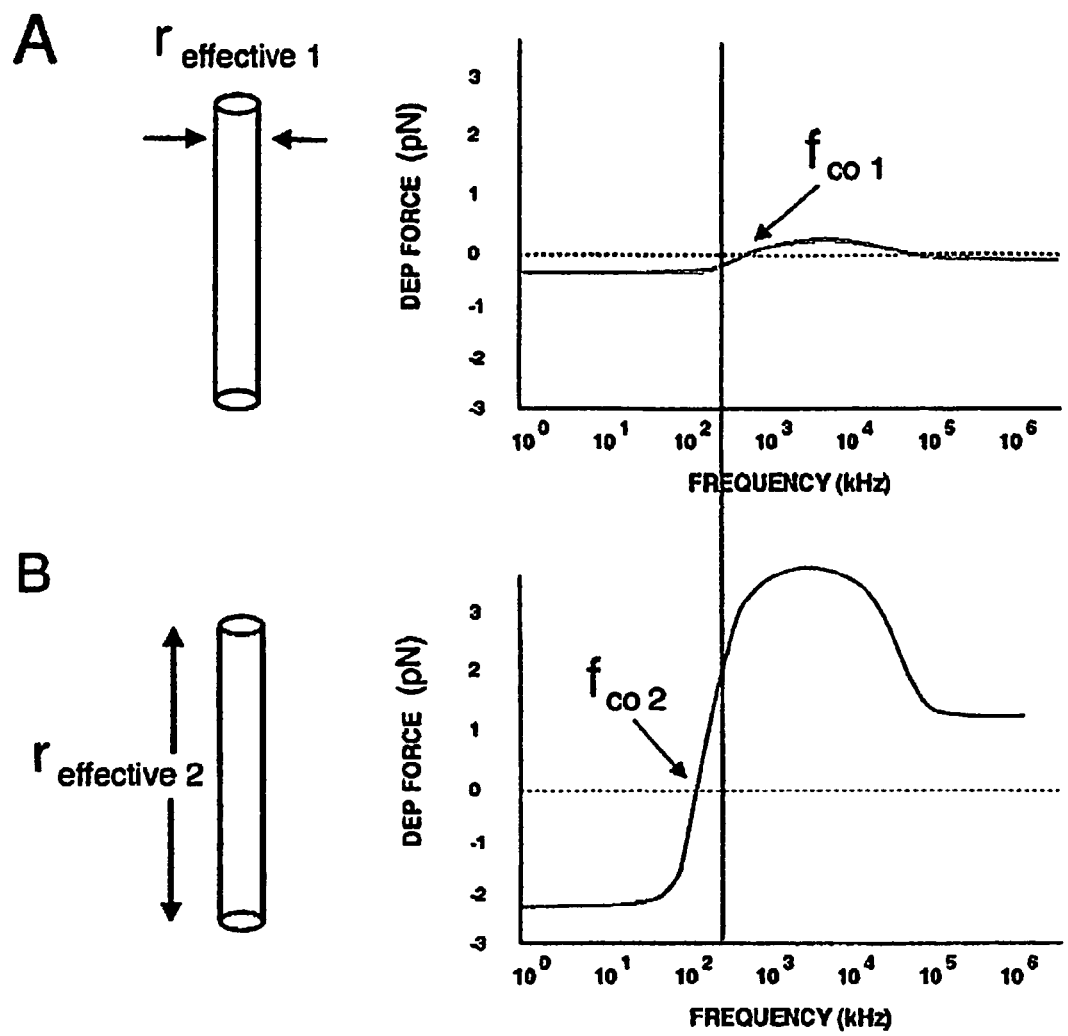
FIG. 18 illustrates a calculation of DEP force on elongated cell structures (e.g., axons) at various frequencies according to specific embodiments of the invention.

FIG. 18 illustrates a calculation of DEP force on elongated cell structures (e.g., axons) at various frequencies according to specific embodiments of the invention. Assuming a typical bilayer cell membrane structure, the DEP crossover frequency, along the short axis of the axon ($f_{co1}$) is predicted to be in the 450 kHz range at 56 mS/m (FIG. 18A). Down the long axis, however, the crossover frequency, $f_{co2}$, is predicted to be in the 80-150 kHz range, depending on the internal ionic conductivity of the axon (FIG. 18B). Thus, with the application of a frequency between $f_{co1}$ and $f_{co2}$, (ex. 300 kHz, red line, FIGS. 18A, B), a DEP force can be generated from a probe that will selectively attract the end of the axon, allowing it to be moved while, at the same time, the sides of the axon will tend to be repelled from the probe.

Retinal Axon Culture Medium for DEP

In some applications it is useful to maintain axons for a period of time in an in vitro media. According to specific embodiments, the present invention can optimize low conductivity media for use with axon (e.g., retinal axon) DEP. For example, the maintenance of mouse retinal axons in culture requires a source of nutrient, the presence of physiological pH, osmolarity, and a temperature of 37 C. Typically, this is achieved by using mammalian culture media such as F12 that contains a bicarbonate-based buffering system, and requires 5% $CO_2$ to maintain a physiological pH.

In some in vitro applications of the invention axon surgery can be carried out on an inverted microscope using a temperature controlled open tissue culture chamber that allows access for MEMS microdevices. To maintain pH under these conditions, the F12 medium was substituted with a $CO_2$ independent medium (CIM, Gibco/BRL). CIM was found to maintain physiological pH in room air, and supported robust axon outgrowth.

In general, it has been found that DEP requires a difference in conductivity between the medium and the internal conductivity of cells. Given that cell internal cytoplasmic conductivities are typically close to 600 mS/m, suspending medium conductivities of around 200 mS/m or less are useful for effective axon DEP. To achieve these low conductivities, in one example, a method of the invention decreases the percentage of CIM culture media, while maintaining the osmolarity in the physiological range using mannitol or a mixture of 8.5% sucrose and 0.3% dextrose. Published studies have found that this type of low conductivity media is able to keep cells healthy for periods of an hour or more (reviewed in (Gascoyne and Vykoukal, 2002)).

Investigations have demonstrated the viability of retinal axons after exposure to low conductivity media. Results showed that retinal axons exposed to low conductivities (19 mS/m) for 60 minutes did not appear to be damaged and in fact continued to grow following their return to standard media. In actual repair, retinal axon exposure to low conductivity DEP medium is anticipated to last only 5-10 minutes.

Experimental Results Showing DEP Manipulation Of Retinal Axons In Culture

Experimental results show that retinal cells and axons in culture can be manipulated using DEP forces. One set of experiments were conducted using a commercial electrode (CE2B75, FHP) consisting of a pair of insulated platinum/iridium wires 12.5 microns in diameter, separated by approximately 10 microns. In these experiments, retinal axon and cells moved in response to positive DEP fields (MHz, 10V amplitude, 10 mS/m). Retinal explants were cultured overnight on laminin-coated coverslips in F12 medium with N2 supplement. After 16 hours, coverslips containing explants with axons were placed in a heated chamber on an inverted microscope. The culture medium was substituted by low conductivity medium (10-60 mS/m, 290 mOsm) formulated by using a combination of CIM, sucrose, and dextrose. The electrodes were positioned using a micromanipulator, and AC electrical current provided by a function generator (HP8116A), and monitored on an oscilloscope. Using 10V amplitude at 1-MHz, axons and cells within 50 microns were attracted towards the electrodes.

Figure 19C:
Figure 26:
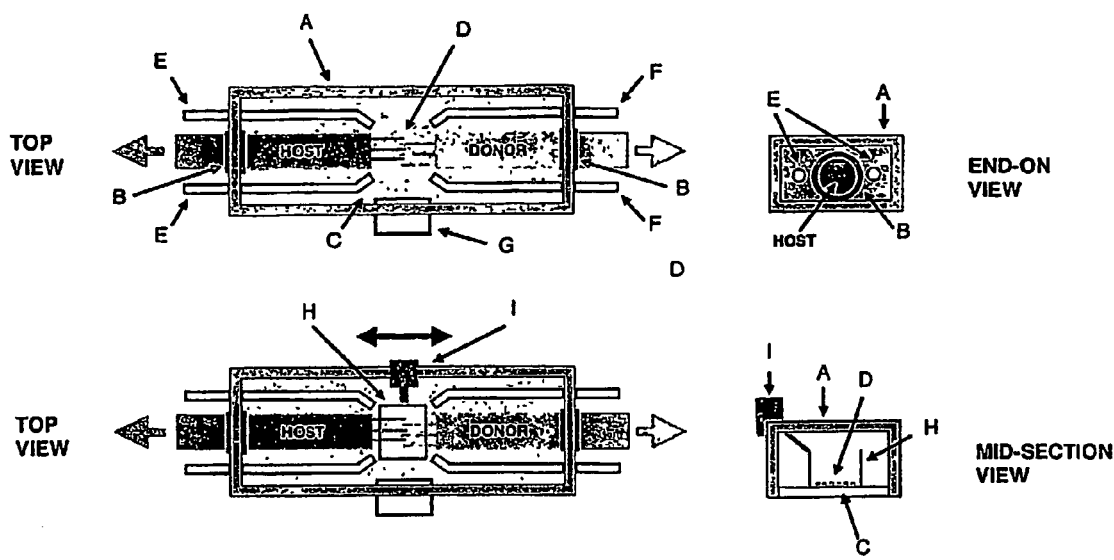
FIG. 26 is a block diagram illustrating an example method and system for performing axon repair on a nerve in a surgical setting showing a surgical frame with a nerve gasket and other mechanisms for holding nerves in place for performing nerve repair according to specific embodiments of the invention.

Further experiments using simple microfabricated MEMS electrodes have shown DEP manipulation of adult axon segments. In these experiments, sciatic nerve segments were isolated and placed in a drop of low conductivity medium (15 mS/m) placed on top of a MEMS planar electrode pair. (FIG. 19A-C) A stimulus of 10 V p-p was delivered at 500 kHz. This stimulus parameter caused axons in the vicinity of the electrodes to move in the direction towards the semi-circular plate electrode. Axons returned to their original location after the stimulus was turned off, likely due to tethering of the axons to the bulk of the nerve segment. These experiments show that microfabricated MEMS electrodes can be used to reliably generate DEP fields. In addition, these studies showed that the DEP effect was localized to a small area in between the electrode pairs. This localized effect is anticipated as DEP forces drop off significantly away from the region of the strongest electrical gradients. The verification of this prediction is significant and indicates that relatively dense arrays of MEMS electrodes can be constructed for precise spatial activation of DEP fields to move only specific axons of interest. According to specific embodiments of the invention, during in vivo nerve repair, a surgical frame as shown in FIG. 26 may be used to temporarily isolate the damaged nerve and/or any donor segments and to introduce a fluid medium with the desired conductivity properties as described herein.

Electrode Module for Axon Manipulation

Figure 20:
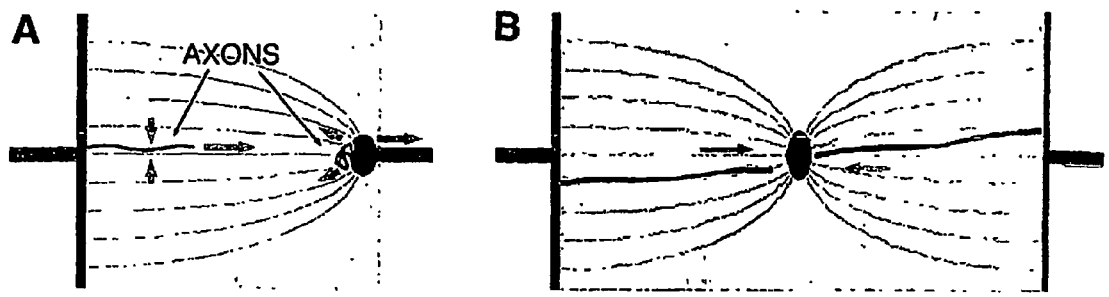
FIG. 20 illustrates behavior of axons in DEP fields according to specific embodiments of the invention showing (A) DEP field created by a pin/probe and one plate electrodes; (B) DEP field created by a pin/probe and two plate electrodes with field lines as illustrated.

One mechanism for providing an inhomogeneous AC electric field for DEP is to use pin and plate electrodes, as shown in FIG. 20A. In this particular configuration, the region of the strongest field is towards the pin electrode. As a result the axon on the left will be stretched out, but the axon on the right will collapse towards the pin electrode. While such a pin and plate electrode configuration is useful for the removal of axon segments from the surgical field, it generally cannot be used to achieve axon alignment. A second configuration is the use of two plate electrodes to provide a homogeneous electric field within which a pin or probe is used to create a field inhomogeneity (FIG. 20B). In this configuration, the strongest electrical fields are found around the probe. As a result, DEP forces stretch out both axons and pull both ends towards the probe.

Either an energized probe or a dielectric probe can be used for axon manipulation in the probe electrode configuration, since both would produce a local field inhomogeneity. However, it has been determined that more control is obtained by using an energized probe, since the signal to the probe may be adjusted as necessary. The precision of axon manipulation using this probe method is determined by the size of the probe tip. Since the diameter of axons is on the order of microns, a microfabricated probe having a tip diameter generally in this same size range is useful. If necessary, two probe tips can be used to bring different axon ends into proximity, then one could be removed so that one probe could create the necessary juxtaposition for axon attachment.

Axon Manipulation Using DEP Electrode Array

According to specific embodiments of the invention, both the pin-plate and the probe electrode configurations are used during axon repair to carry out different axon manipulations. Referring to FIG. 16, the removal of segments b and c is performed using a interdigitated pin-plate configuration as shown in FIG. 16B. In this particular example interdigitated pin-plate configuration, three different pin/probe-plate electrode pairs are shown for each side of the surgical area. The inner most pair can be activated for the initial movement of a segment away from the central region, with the subsequent outer pairs moving segments further away from the field.

The alignment of the ends of segments a and d is accomplished using the electrode configuration in FIG. 16B, where the central pin/probe is shown as being part of the nanoknife. In specific embodiments, both electrode configurations are patterned onto the ends of beams within an electrode module and the two electrode arrays, each connected to a beam, are positioned along either side of the MEMS nanoknife. During use, the electrode arrays are located in a fluid medium above the axons and the cutting surface. The distance between the axons and the electrode arrays in one example implementation is fixed at 30 microns, though moveable arrays and different dimensions are possible according to specific embodiments of the invention. In another configuration, the electrodes are below or embedded within the bottom surface of the culture dish coverslip (in vitro) or the bottom of the surgical frame (in vivo) and in these embodiments, there may not be need for electrode arrangements held on side carrier arms as shown in FIG. 16.

Interdigitated Pin-Plate Electrode Configuration for Moving Segments b and c

Figure 21A:
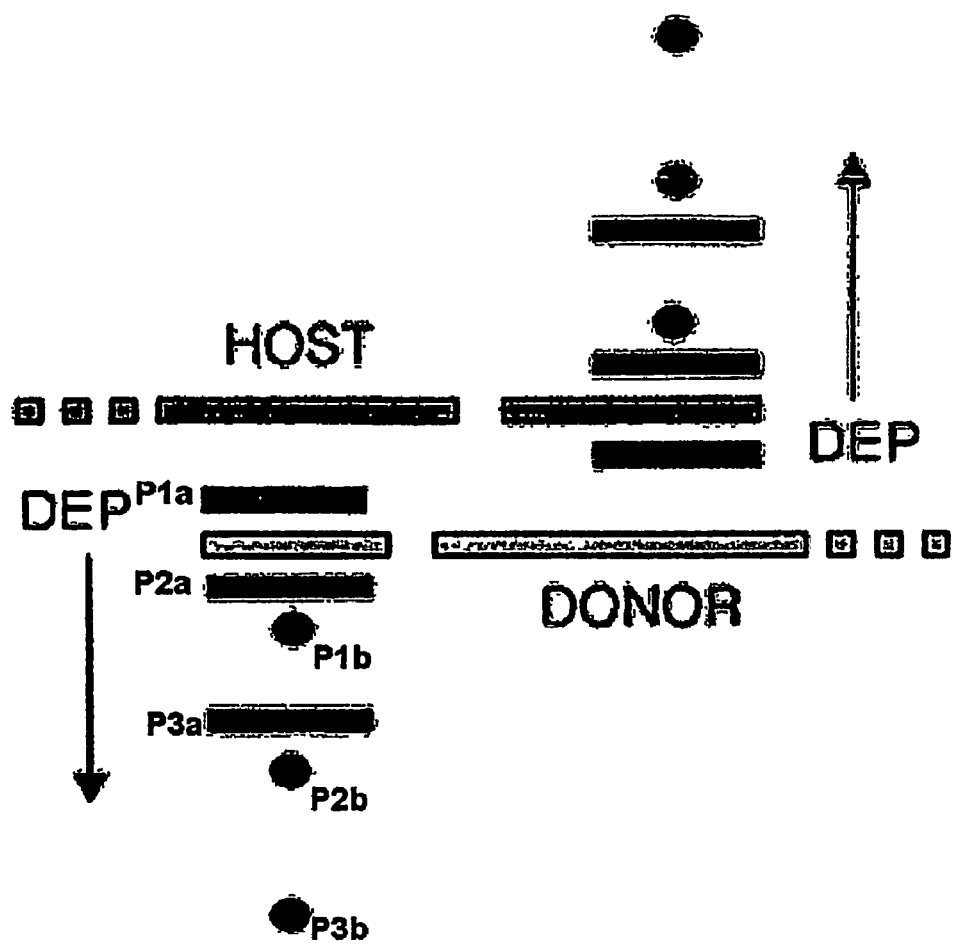
FIG. 21 is a block diagram illustrating use of interdigitated pin-plate electrode configuration to move cell portions (e.g., axon segments b and c) showing (A) position of electrodes with respect to the four axon segments; (B) movement of axon segments b and c from original positions after DEP.
Figure 21B:
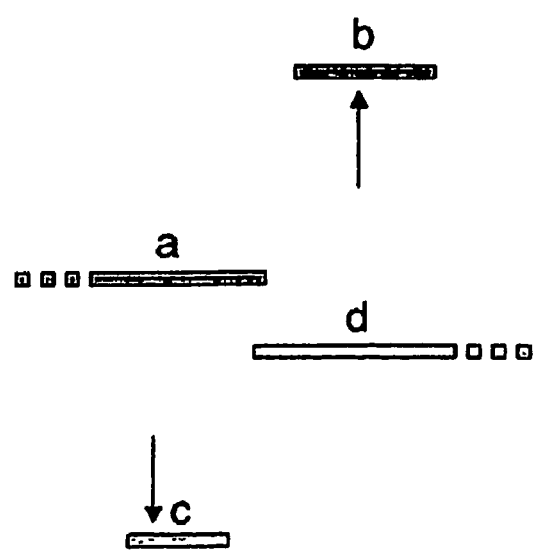

DEP forces generated by a series of interdigitated pin-plate electrodes are used to remove axon segments b and c from the surgical field. At their starting positions, axon segments b and c are located in this example below and in between the first pairs (P1$a$ and P1$b$) of pin/probe-plate electrodes (FIG. 21A). The activation of DEP forces using this electrode pair will result in the net movement of segments b and c towards the first pin position. (Due to their location away from the electrical fields and DEP forces, segments a and d are minimally affected.) Activation of the second pairs (P2$a$ and P2$b$) of pin-plate electrodes results in additional movement of b and c away from their original positions. Sequential activation of optional further pin/probe-plate electrodes (e.g., P3$a$ and P3$b$) results in the translocation of b and c away from the surgical field and prevent their interference with the axon fusion process (FIG. 21B).

Electrode Configuration for DEP Axon Alignment

Figure 22:
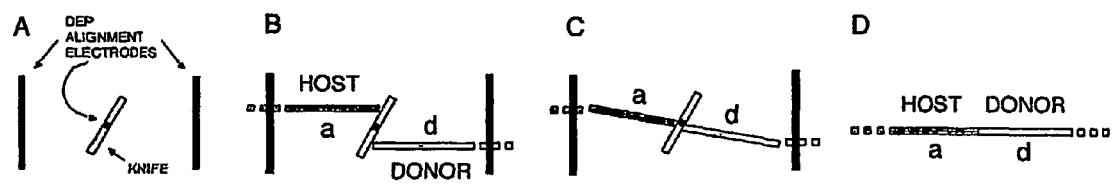
FIG. 22 is a block diagram illustrating axon DEP alignment and electrofusion according to specific embodiments of the invention showing (A) electrode configuration for axon alignment; (B) electrode over axon segments to be aligned; and (C) DEP induced alignment of the ends of axon segments with axon ends in contact at the conducting element at the center of the MEMS knife; and (D) host and donor axons joined after electrofusion.

The probe electrode configuration (FIG. 22A) is used to align the ends of the axons segments to be fused (Segments a, and d). In this case, the two plate electrodes are oriented perpendicular to the long axis of the axon segments to be manipulated (FIG. 22B). A central probe creates a field inhomogeneity and serves as a node for alignment and attachment of the axon segments at their ends. In the configuration shown below, the nanoknife itself is modified so that an energized element is placed at the center of the knife, in the region overlying the area between segments a and d. Activation of the probe and the plate electrodes causes the ends of axon segments a and d to come together (FIG. 22C).

The use of a modified MEMS knife with a conducting node that serves as a probe electrode is convenient because the cutting procedure prepositions the conducting node in the correct position in between segments a and d. One potential caveat to this arrangement is that the non-conducting portions of the knife may also create a field inhomogeneity and may lead to the ends of axon segments a and d to attach to other regions of the knife and not to each other. One solution in this situation in specific designs is to enable the platform to withdraw the knife after use and insert an independent probe to mediate axon alignment.

In the DEP methodology described above, the spacing between the host and donor axons influences the spacing required between electrodes and the parameters necessary for effective DEP axon movements. One possible electrode configuration to accommodate a range of axon spacings is an addressable electrode grid, so that appropriate electrodes within the grid can be selected to deliver DEP force to any host and donor axon pair. Such a grid can have many more selectable pin/probe and/or plate electrodes which can be activated during a procedure to move axon elements as desired. An addressable grid may be placed in the medium above the axons or below or embedded within the bottom coverslip or the bottom of the surgical frame.

Figure 23:
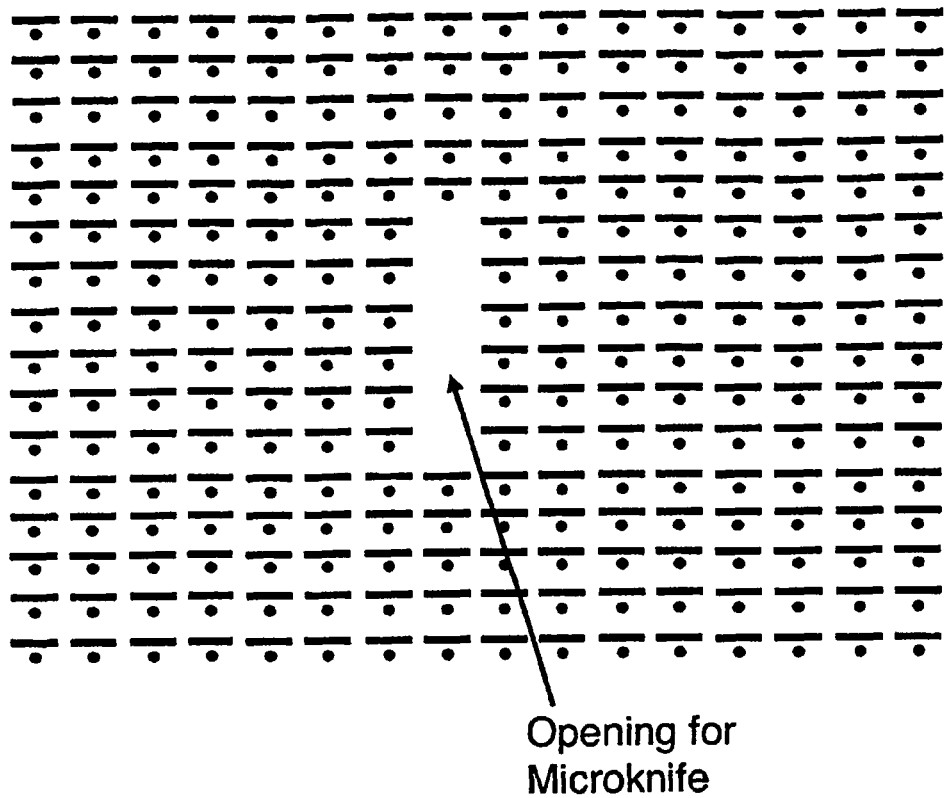
FIG. 23 is a block diagram illustrating an example arrangement of electrodes in an addressable grid for manipulating axons and/or other small objects using DEP according to specific embodiments of the invention.

FIG. 23 is a block diagram illustrating an example arrangement of electrodes in an addressable grid for manipulating axons and/or other small objects using DEP according to specific embodiments of the invention. In the example shown, a space is left for placement of the axon knife, though in other examples, this space will not be needed, for example where the grid is below the items to be manipulated and the knife above. As discussed herein, electrodes in such an addressable grid arrangement can be placed under and/or over objects to be manipulated (e.g., axons), but most typically will be placed underneath axons and arranged to allow viewing of axons in relationship to the grid. In some embodiments, it will be desirable to place electrodes both under and over structures to be manipulated. Such a grid can be fabricated using techniques known for fabricating solid state electronics elements, as well known in the integrated circuit art. Various strategies and/or structures for addressably applying energy signals to such a grid are also well known in the integrated circuit art, and any such strategy can be employed in an addressable grid according to specific embodiments of the invention. Such an addressable grid of electrodes can a few and up to hundreds of addressable electrodes, depending on specific embodiments. On example discussion of an electronic circuit configuration for addressing different elements is that found in U.S. Pat. No. 6,582,660.

9. Fusion

After axon cutting and alignment, the opposing axon segments are fused together to achieve functional continuity. Cell fusion in biology is most commonly used in the creation of hybridoma cells for monoclonal antibody production. A number of methods can be used to promote cell fusion. These include chemical fusion using polyethylene glycol (PEG), laser induced fusion, and electrofusion. Due to its low cost and ease of use, PEG is a popular fusogen for hybridoma cell production. However, PEG is well known to have toxic effects on cells. Since PEG is typically used in instances in which millions of cells are available for fusion, substantial cell loss and low viability after fusion is acceptable, if a few immortal cells remain.

An alternative method that has been described is laser cell trapping combined with laser induced membrane fusion (Ohkohchi et al., 2000). In this approach, lasers are then used for optical cell trapping and to bring two cells into contact with one another. Once in position, a different laser is used to induce breakdown of the cell-cell membrane contact region. A fusion rate of 38% was reported. This laser fusion technique however still required the addition of 5% PEG, as the fusion rate without PEG was 0%. The use of laser trapping and fusion requires a great deal of operator involvement and skill and a substantial investment in specialized optical equipment. The integration of optical laser cell trapping and fusion into a MEMS axon surgery platform is not easily implemented at the present time.

Electrofusion

Thus, while a number of cell fusion methods may be adapted in specific embodiments of the invention, a presently preferred method is electrofusion. Electrofusion involves the use of electrical pulses to create the transient breakdown of the cell membrane and the formation of pores that are unstable and eventually reseal (Neil and Zimmermann, 1993). If the pores are formed in the region of contact between neighboring cells, fusion between the two cells will occur. The threshold voltage across a membrane required for this electrical breakdown is approximately 1 V. In cell culture, the typical field strengths required to generate 1 V across membranes are in the range of 2-8 kV/cm (Bates et al., 1987; Neil and Zimmermann, 1993), usually delivered using 24 rectangular pulses of 10-100 micro seconds each.

According to specific embodiments of the invention, electrofusion can be pre-programmed to automate axon fusion. In addition, MEMS electrodes can be used for both DEP and electrofusion. Such electrodes are easily fabricated and incorporated into MEMS devices and with DEP used to align axons, electrodes will already be conveniently placed to deliver electrical pulses for axon fusion. The pairing of DEP with electrofusion permits both steps in the axon repair sequence to be accomplished using electrodes, thus simplifying the design and operation of the MEMS axon surgery platform. Use of a MEMS axon surgery platform that operates at the level of individual axons to systematically initiate axon fusion that does not necessarily involving problematic chemical fusogens is also desirable.

Axon End Forces and Electrofusion

According to specific embodiments, a sequence of DEP followed by electrofusion is used to join axons. Typically in cell electrofusion, 5-100 volts p-p amplitude are used to create electrical fields in the range of 1-10 kV/cm to disrupt the membranes in the high field regions where the cells touch. This is usually delivered in the form of one to several voltage pulses of 10-200 microseconds duration at 1 Hz. As the ends of the two axons approach one another, they are coupled into the electrical field and exhibit attractive end-forces. Once the axons have been brought into juxtaposition, the central pin/probe can be de-energized and removed (e.g., lifted using actuators) and fusion signals applied from the plate electrodes distal to the desired junction can be energized so as to bring about a DEP force directly between the axon ends (FIG. 22D).

Figure 24:
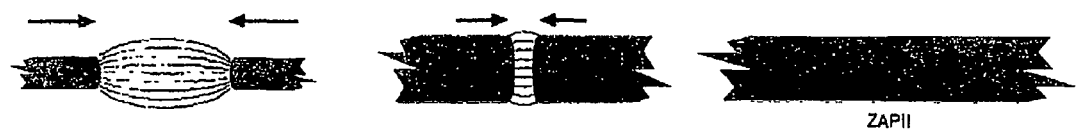
FIG. 24 is a block diagram illustrating effects of end forces as the ends of axons approach one another.

FIG. 24 is a block diagram illustrating end forces as the ends of axons approach one another. At a given distance, the ends couple with the electrical field to create a DEP force. This DEP force brings the axon ends into direct contact with one another. At this stage, electrofusion is initiated.

Figure 25:
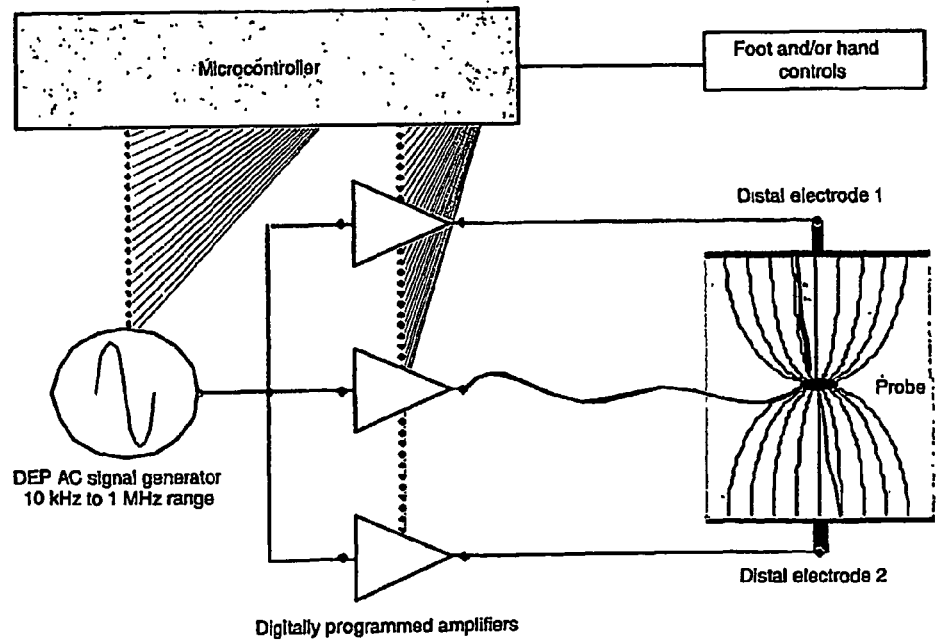
FIG. 25 is a block diagram illustrating an example of a network of oscillator and amplifiers to control delivery of DEP and electrofusion according to specific embodiments of the invention.

The signals for axon DEP manipulation and axon electrofusion need to be readily controlled during the repair process. The switching from DEP to electrofusion can be achieved through a digitally controlled oscillator and a simple network of digitally controlled amplifiers as shown in FIG. 25. This design allows the voltages on both the distal plate electrodes and the probe to be changed immediately to deliver DEP or electrofusion parameters on demand from foot and/or hand controls.

Biological Manipulations to Assist Fusion

In further embodiment, fundamental cell biological processes can be used in parallel with electrofusion to enhance axon repair. One example is the promotion of microtubule assembly at the axon splice junction. Microtubule assembly can be affected by pharmacologic agents, which either promote tubulin polymerization or trigger de-polymerization. One scheme is to depolymerize microtubules prior to axon electrofusion followed by the application of agents such as low dose taxol to enhance microtubule polymerization across the splice junction. A second example is the harnessing of intrinsic mechanisms that cells and axons use for self-sealing. Physical disruptions in the plasma membrane of cells and axons are patched by internal membrane vesicles that are directed to the site of injury in a calcium dependent process (Bi et al., 1995; McNeil and Steinhardt, 1997; Detrait et al., 2000). The activation of the calcium mediated self-sealing mechanism around the site of electrofusion may help axon membrane reseal at the splice junction.

Experimental Results Showing Effective Fusion

Investigations have shown cytoplasmic continuity to show effective fusion using transgenic mice in which the gene encoding Green Fluorescent Protein (GFP) has been introduced into the germ line, and GFP protein is produced in all the cells of the animal (Okabe et al., 1997). Retinal axons from GFP transgenic mice contain soluble GFP and after excitation exhibit green fluorescence that can be easily visualized on a fluorescence microscope. Axons from non-transgenic wild-type mice do not exhibit fluorescence under the same wavelength excitation. The successful fusion of a GFP axon with an axon segment not expressing GFP has shown passive diffusion of GFP into the non-transgenic axon and caused this axon segment to become visible. Experimental results have shown that electrofusion can be used to fuse retinal axons in culture leading to the spread of soluble GFP between axons. Electrofusion was carried out in normal media or in low conductivity media (23 mS/m) containing 0.3 mM $CaCl_2$ using the electrodes employed for axon DEP. 10-30 rectangular pulses each of 5 V and 250 µsec duration were applied at roughly 1 Hz to deliver electrical fields of around 1 kV/cm.

Restoration of plasma membrane continuity between axon segments can also be demonstrated using lipophilic membrane fluorescent dyes. The carbocyanine dye, DiI is brightly fluorescent, shows good stability, and is known to diffuse readily within the lipid bi-layer. Similar to the situation for GFP axons described above, the restoration of plasma membrane continuity between two axon segments has be shown to allow the diffusion of DiI molecules across the repair site. DiI labeled retinal explants were mixed with unlabeled explants and placed overnight on laminin coated coverslip dishes. After 24-48 hours, pairs of DiI and non-DiI axons that crossed over one another were selected for electrofusion. As with GFP axons, electrofusion was carried out in low conductivity media (23 mS/m) containing 0.3 mM $CaCl_2$ using the electrodes employed for axon DEP. 10-30 pulses each of 5 V amplitude and 250 µsec duration were applied at 1 Hz to deliver electrical fields of around 1 kV/cm. The spread of lipophilic DiI molecules into the unlabeled axon of the axon pair subjected to electrofusion was examined over a one and a half hour period using fluorescence microscopy. DiI fluorescence was seen in the originally unlabeled axon within 15 minutes after electrofusion. Over 90 minutes, DiI fluorescence spread 100 microns along the axon.

Axon electrofusion success can be further enhanced by the use of electrodes of a size more commensurate with retinal axons that are 1-2 microns in diameter and/or the use of enzyme pre-treatments prior to electrofusion to digest away extracellular material or membrane proteins at regions of axon contact. Retinal axons express transmembrane glycoproteins such as Neural Cell Adhesion Molecule (NCAM) that govern intercellular distances by their degree of glycosylation. Glycosylation may be removed by neuraminidase, and proteins can be cleaved by proteases. Proteases have been used to treat cells prior to hybridoma electrofusion, and result in an increased fusion rate.

Using Mitochondria Movement to Shown Fusion

As an important function of axons is the transport of proteins and organelles between the neuron cell body and synaptic terminals, tracking transport of membranous organelles such as mitochondria, which move at rates of about 0.5 microns/sec in axons is another mechanism that can be used to demonstrate effective fusion. Observations of mitochondrial movement across a repaired axon junction using transgenic mouse line in which GFP is expressed exclusively in mitochondria have indicated restoration of the microtubule cytoskeleton and reconstitution of an important transport function of axons.

10. Axon Repair In Vivo

Sources for Donor Axons

Donor axons to be used as fusion partners can be obtained from autologous nerves. In current medical practice, peripheral nerve injuries are occasionally treated by surgical placement of a nerve graft. In these instances, autologous nerve segments are commonly harvested from the antebrachial nerves of the arm or the sural nerve at the back the calf to serve as connective tissue conduits (Millesi, 1991). At present, the axons within the harvested nerves are not utilized. In MEMS axon surgery, the harvested nerve segments will provide a source of healthy donor axon segments to be used in axon fusion. Axons will be separated from the surrounding connective tissues by enzymatic digestion of collagen and other means to eliminate the oligodendrocytes and Schwann cells. The exposed axons are then ready for cutting, alignment, and fusion.

Example Nerve Tissue Dissociation By Enzymatic Digestion And Other Means

According to specific embodiments of the invention, the application of direct cellular repair to adult nerve tissues requires the isolation of individual axons from intact nerves. An adult nerve generally consists of as many as tens of thousands of individual axons, which are bundled together with a hierarchical network of connective tissues. Additionally, many axons are ensheathed by Schwann cells that form the myelin insulation that facilitates signal propagation.

According to specific embodiments of the invention, obtaining axons for cutting and manipulation requires a careful treatment to digest the various components of connective material holding the nerve processes together and reveal isolated or nearly isolated axons while minimizing harm to the axons and nerve cells themselves. In order to accomplish this, in specific embodiments, a dissociation cocktail with the goal of abolishing the cell-cell adhesions and breaking the connective matrices of the nerve is used.

Different combinations of substances in different proportions can be used for such a cocktail, and cocktail combinations that are more preferable to presently preferred combinations may be developed, in particular for particular applications.

In one example specific cocktail, $Ca^{2+}$ ions were withheld and inhibited by the calcium chelator EGTA to block $Ca^{2+}$-dependent adhesion mechanisms. A cocktail of enzymes was prepared in $Ca^{2+}$ and $Mg^{2+}$-free, glucose-containing Hanks buffered saline in the following approximate concentrations:

| | |
|---|---|
| 0.50% (w/v) | Collagenase I |
| 0.50% | Collagenase III |
| 0.25% | Hyluronidase |
| 20 units/mL | Papain |
| 0.25% | Elastase |
| with 3 mM of | EGTA |

To demonstrate the performance of this digestion cocktail, sciatic nerves from adult mice were removed and maintained at 37° C. The cocktail was applied to the nerve soon after removal from the animal either in static incubation or under flow to provide some fluid mechanical agitation. Both approaches resulted in a dissociation of individual fibers, both myelinated and unmyelinated, from a previously intact nerve bundle. It was possible to observe distinct dissociated fibers, especially near the periphery of the nerve.

Re-Myelination of Repaired Axons

Schwann cells or oligodendrocyte glia cells extend cytoplasmic protrusions to form myelin around axons to enhance electrical conduction. Thus, re-myelination of axons after MEMS axon surgery is likely to be important for enhancing functional recovery. Research indicates that transplanted cells can help re-myelinate axons. Olfactory ensheathing cells (which resemble Schwann cells), oligodendrocytes, and oligodendrocyte precursor cells have all been demonstrated to be effective in providing myelin for axons in vivo after experimentally induced demyelination (Blakemore and Franklin, 2000; Franklin, 2003). A recent study in fact indicates that adult stem cells injected intravenously can re-myelinate CNS axons (Pluchino et al., 2003), potentially providing a simple and convenient cell delivery method without requiring intracranial access. Cell transplantation is currently being tested in clinical trials as a treatment for de-myelinating diseases (Stangel and Hartung, 2002). According to specific embodiments of the invention, nerve repair surgery can be further combined with any effective axon re-myelination techniques, with a presently preferred method comprising a cell replacement strategy.

Number and Which Axons to Repair

Peripheral nerves and axon tracts in the CNS often contain large populations of axons numbering in the thousands. An important point to consider is how many axons need to be repaired to obtain functional recovery. Results from studies aiming to promote CNS axon regeneration can serve as a guide. Following spinal cord lesions in rodents, the regeneration of 100-200 axons has been reported to correlate with some recovery of function (Coumans et al., 2001; Merkler et al., 2001; Bradbury et al., 2002). This finding is thought to reflect the potential for substantial plasticity in the injured nervous system and indicates that it may not be necessary to repair all axons within a PNS nerve or a CNS axon tract. The immediate repair of a subset of axons should provide a sufficient degree of functional recovery to alleviate the disability normally associated with nerve injuries.

A characteristic feature of both CNS axon tracts and PNS nerves is the topographic organization of axons. Throughout the nervous system, axons that originate from adjacent neurons tend to run together and maintain their neighbor relationship within a nerve or axon tract. The location and function of specific axons within nerves and axon tracts is generally well preserved between individuals. Furthermore intra-operative electrophysiological testing can also be used in many cases to assist in the identification of axons. Thus, in a clinical setting, the selection and alignment of axons for repair can be based on knowledge of the location of specific axon tracts, the fact that adjacent axons typically subserve the same neurological function, and data obtained from electrophysiological testing.

In clinical applications, the careful selection of axons to be repaired is expected to contribute significantly to surgical success. One strategy is to focus on damaged axons that are physically most accessible for MEMS assisted repair. In addition, it would be useful to target large diameter axons for repair, since these axons mediate motor and somatosensory function, while smaller axons carry pain and temperature sensation. MEMS axon repair may also be more easily accomplished in larger axons than in small axons less than a micron in diameter. A further consideration is to identify situations where the reconnection of a subset of axons can make a large difference in the clinical management and in the patient's quality of life. An example is the restoration of partial movement in the hand and digits, which would greatly impact how tetraplegic patients interact with their environment. A second example is the repair of axon pathways mediating bladder control. After spinal cord injury, loss of voluntary control of voiding leads to urinary retention and eventually incontinence (Yoshimura et al., 2000). Management by catheterization leads to urinary tract infections, which is a major source of morbidity in these patients (Biering-Sorensen, 2002). Recovery of some degree of bladder control would contribute significantly to their quality of life. The development of MEMS based axon repair, matched with a well thought out surgical plan and realistic expectations, can lead to clinical success.

While aspects of the present invention can be performed with each step involved in axon repair done by operating a separate tool, each independently mounted on its own positioner (similar to probe stations for testing integrated circuits), such an arrangement is bulky and inefficient and represents a less preferred embodiment. Thus, with an assembled MEMS surgical platform according to specific embodiments of the invention reduces positioning time and can achieve a degree of miniaturization that allows for more effective repairs at the cellular level.

11. Integration of MEMS Axon Platform Into the Surgical Field

MEMS axon surgery takes place in a sterile surgical field established by a surgeon. A frame isolates and stabilizes the nerves or region of the CNS to be operated on and provides a mechanical anchor for the MEMS axon surgical platform and other necessary microsurgical tools. Once the donor nerve and axons are in place, the surgeon positions the MEMS platform appropriately to initiate axon cutting, alignment, and repair. MEMS assisted axon repair according to specific embodiments of the invention can thus use existing surgical protocols for the harvesting of donor nerves and some of the steps for a conventional nerve graft procedure. The critical difference is that rather than manually suturing the nerve connective tissues, a multifunctional microdevice is used to reconnect individual axons.

12. Operation of the Surgical Frame

FIG. 26 is a block diagram illustrating an example method and system for performing axon repair on a nerve in a surgical setting showing a surgical frame with a nerve gasket and other mechanisms for holding nerves in place for performing nerve repair according to specific embodiments of the invention. The host nerve is isolated and prepared for axon surgery. The donor nerve is harvested by the surgeon and prepared for axon surgery. The ends of both the host (orange) and donor (blue) nerves are positioned within a surgical frame (A). Both nerves are held in place using a gasket (B) and rest on the bottom plate of the surgical frame (C). At this point, the nerves and submerged within a physiological saline solution. The axons segments from the host and donor nerves (D) are located within the central portion of the surgical frame. Inflow tubing (E) is used to bring in other solutions necessary during axon surgery. These include low conductivity dielectrophoresis suspension medium, and/or medium containing other chemical or biological agents to assist the repair process. Outflow tubing (F) is used to remove media from the interior of the surgical frame. Optical waveguide(s) (G) are built into the surgical frame to provide lighting and for optical monitoring. The MEMS axon repair platform (H) is positioned over the host and donor axons to perform axon trimming, dieletcrophoresis, and electrofusion. The position of the MEMS axon platform is adjustable and can be precisely positioned using a micromanipulator (I) that is attached to the surgical frame.

A number of different techniques can be used to create the MEMS components discussed and described herein. One example and presently preferred technique involves fabricating the modular components as described herein on flat wafers, generally of silicon, as is known in the electronic circuits art.

13. Other Embodiments

The invention has now been described with reference to specific embodiments. Other embodiments will be apparent to those of skill in the art. In particular, a number of novel methods and apparatus have been described herein in the context of a novel method for nerve repair. It should be understood that the invention in specific embodiments encompasses any of these novel elements separately and used in any other suitable application. The invention also comprises the general methods that will be understood from the description herein. Thus, it is understood that the examples and embodiments described herein are for illustrative purposes and that various modifications or changes in light thereof will be suggested by the teachings herein to persons skilled in the art and are to be included within the spirit and purview of this application and scope of the claims.

In particular, methods for nerve repair by repairing axons should be understood as independent of any particular surgical platform for performing same. While a particular modular platform is shown other configurations of systems to perform one or more methods as described herein are possible and may prove to be preferable in specific situations. For example, many different configurations for electrodes are possible, including electrodes that are embedded and/or integrated into a bottom coverslip rather than positioned on electrode arms as shown. In other embodiments, systems that allow lateral positioning of a nanoknife in relation to a surgical platform may be developed to allow for repair of multiple axons while holding the surgical frame stationary. In further embodiments, systems having electrode grids that allow for sequential controlled movement of multiple axons may be used.

All publications, patents, and patent applications cited herein or filed with this application, including any references filed as part of an Information Disclosure Statement, are incorporated by reference in their entirety.

What is claimed:

1. A method of repairing a damaged nerve in a living organism comprising:
    selecting one or more axons in said damaged nerve;
    harvesting a donor axon segment;
    positioning said donor axon segment at a severed location of a selected axon by applying a dielectrophoresis signal in proximity of one or more of said donor axon or said selected axon; and
    inducing fusion of said donor axon segment said inducing selected from the group consisting of applying an electric signal in proximity of one or more of said donor axon or said selected axon, applying a laser in proximity of one or more of said donor axon or said selected axon, and manipulating cell biological processes to enhance axon repair in proximity of one or more of said donor axon or said selected axon.

2. The method of claim 1 further comprising:
    cutting one or more ends of said donor axon and/or said selected axon.

3. The method of claim 1 further comprising:
    digesting one or more nerve portions to allow manipulation of individual axons.

4. The method of claim 1 further comprising:
    using a MEMS axon surgical platform enabling precise manipulation of axons of less than one and up to a few microns in diameter.

5. The method of claim 4 further wherein:
    said MEMS axon surgical platform enables manipulation of axons directed by a human surgeon.

6. The method of claim 1 wherein said living animal comprises a human.

7. The method of claim 1 wherein said living animal comprises a mammal.

8. The method of claim 1 wherein said inducing further comprises:
    applying a laser in proximity of one or more of said donor axon or said selected axon.

9. The method of claim 1 wherein said inducing further comprises:
    manipulating cell biological processes to enhance axon repair in proximity of one or more of said donor axon or said selected axon.

10. A method of repairing a damaged nerve in a living organism comprising:
    selecting one or more severed axons in said damaged nerve;
    positioning one or more of said selected severed axons in close proximity to one or more corresponding severed axons on another side of said damaged nerve by applying a dielectrophoresis signal in proximity of one or more of said donor axon or said selected axon; and
    inducing fusion of said donor axon segment said inducing selected from the group consisting of applying an electric signal in proximity of one or more of said donor axon or said selected axon, applying a laser in proximity of one or more of said donor axon or said selected axon, and manipulating cell biological processes to enhance axon repair in proximity of one or more of said donor axon or said selected axon.

11. The method of claim 10 further wherein:
said selecting, positioning, and inducing are performed without determining whether a corresponding severed axons is matched to axon segments to which they were attached before becoming severed.

12. The method of claim 10 further comprising:
using a nanoknife to cut said one or more severed axons prior to said inducing.

13. The method of claim 10 further comprising:
placing a three-dimensional microstructure over an area containing said axon;
said three-dimensional microstructure comprises:
one or more nanoknives used for cutting axons;
one or more actuators for moving said nanoknives; and
one or more effector electrodes for moving axons,
said three-dimensional microstructure is smaller than approximately one cubic millimeter.

14. The method of claim 13 further wherein:
said three-dimensional microstructure is smaller than approximately 100 cubic millimeters.

15. The method of claim 13 further comprising:
placing said three-dimensional microstructure in a surgical frame, said surgical frame comprising one or more gaskets for holding one or more nerves to be repaired;
said three-dimensional microstructure and said surgical frame comprising one or more microfluidic channels for delivering reagents; and
said three-dimensional microstructure comprising one or more waveguides to enable optical monitoring, visualization, and/or use of light sources.

16. The method of claim 13 further comprising:
moving an axon segment using a pin/probe and plate electrode pair operably connected with said microstructure such that a region of strongest field is towards the pin electrode thereby stretching an axon towards said pin/probe electrode.

17. The method of claim 10 further comprising:
moving an axon segment by precisely positioning arrangements of micro-electrodes near to said axon segment; and
applying electrical signals precisely to particular electrodes to effect precise movements and/or manipulations.

18. The method of claim 17 wherein said precisely positioning of arrangements of electrodes comprises positioning an addressable grid of electrodes above and/or below said axon segment and further comprising:
observing said axon segment in relation to said addressable grid of electrodes;
selecting one or more electrodes that will effect a desired movement of said axon segment; and
applying a predetermined energy signal to said one or more electrodes; and further comprising:
observing an induced movement of said axon segment in relation to said addressable grid of electrodes;
selecting an additional one or more electrodes that will effect a desired further movement of said axon segment; and
applying a predetermined energy signal to said additional one or more electrodes.

19. The method of claim 10 wherein said inducing further comprises: applying a laser in proximity of one or more of said donor axon or said selected axon.

20. The method of claim 10 wherein said inducing further comprises:
manipulating cell biological processes to enhance axon repair in proximity of one or more of said donor axon or said selected axon.

* * * * *